United States Patent
Kocis et al.

(10) Patent No.: US 11,077,095 B2
(45) Date of Patent: Aug. 3, 2021

(54) METHODS FOR TREATING NEURODEGENERATIVE DISORDERS

(71) Applicant: Alzheon, Inc., Framingham, MA (US)

(72) Inventors: Petr Kocis, Framingham, MA (US); Martin Tolar, Framingham, MA (US); John Hey, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 0 days.

(21) Appl. No.: 16/488,327

(22) PCT Filed: Feb. 23, 2018

(86) PCT No.: PCT/US2018/019347
§ 371 (c)(1),
(2) Date: Aug. 23, 2019

(87) PCT Pub. No.: WO2018/156845
PCT Pub. Date: Aug. 30, 2018

(65) Prior Publication Data
US 2019/0374514 A1   Dec. 12, 2019

Related U.S. Application Data

(60) Provisional application No. 62/463,421, filed on Feb. 24, 2017.

(51) Int. Cl.
*A61K 31/4196* (2006.01)
*A61K 31/426* (2006.01)
*A61K 31/44* (2006.01)
*A61P 25/28* (2006.01)
*A61K 31/433* (2006.01)
*A61K 31/505* (2006.01)

(52) U.S. Cl.
CPC ........ *A61K 31/4196* (2013.01); *A61K 31/426* (2013.01); *A61K 31/433* (2013.01); *A61K 31/44* (2013.01); *A61K 31/505* (2013.01); *A61P 25/28* (2018.01)

(58) Field of Classification Search
CPC ... A61K 31/4196; A61K 31/426; A61K 31/44
See application file for complete search history.

(56) References Cited

FOREIGN PATENT DOCUMENTS

| WO | 96/28187 A1 | 9/1996 |
|---|---|---|
| WO | 96/39129 A1 | 12/1996 |
| WO | 2005/000288 A2 | 1/2005 |

OTHER PUBLICATIONS

Young et al. Screening and classifying small-molecule inhibitors of amyloid formation using ion mobility spectrometry-mass spectrometry. Nat Chem. 7(1):73-81 (2015).
Caragounis et al. Differential modulation of Alzheimer's disease amyloid beta-peptide accumulation by diverse classes of metal ligands. Biochem J. 407(3): 435-50 (2007).

*Primary Examiner* — Samira J Jean-Louis
(74) *Attorney, Agent, or Firm* — McCarter & English, LLP; Steven G. Davis; Michael J. DeGrazia

(57) ABSTRACT

Methods of treating a disease characterized by amyloid aggregates are provided herein.

4 Claims, No Drawings

METHODS FOR TREATING NEURODEGENERATIVE DISORDERS

RELATED APPLICATIONS

This application is a 35 U.S.C. § 371 national stage filing of International Application No. PCT/US2018/019347, filed Feb. 23, 2018, which claims priority to U.S. Provisional Application No. 62/463,421, filed Feb. 24, 2017, the entire contents of each of which are incorporated herein by reference.

BACKGROUND

Alzheimer's disease (AD) is a progressive degenerative disease of the brain primarily associated with aging. Prevalence of AD in the United States today is close to 5.1 Million. It was estimated that about one in ten individuals over 65 and nearly half of those over 85 are affected by Alzheimer's disease. Approximately 360,000 patients will be diagnosed with AD each year in the United States alone. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: beta amyloid plaques (neuritic plaques) and neurofibrillary tangles. Individuals with AD exhibit characteristic beta-amyloid deposits in the brain (beta amyloid plaques) and in cerebral blood vessels (beta amyloid angiopathy), and later also by abnormally phosphorylated tau protein (neurofibrillary tangles). Recent AD research suggests that soluble oligomeric Aβ constitute main neurotoxic species.

Amyloid plaques and other amyloid and amyloid-type aggregates are also characteristic of other diseases, such as Down's syndrome dementia, Parkinson's Disease, Acute macular degeneration (AMD), glaucoma, Inclusion Body Myositis (IBM), traumatic brain injury, Lewy Bodies dementia, Huntington's disease, Nieman-Picks Type C, Cerebral Amyloid Angiopathy (CAA), Creutzfeldt-Jakob disease, AA Amyloidosis, AL Amyloidosis, ATTR amyloidosis, Familial amyloid polyneuropathy (FAP), Familial amyloid cardiomyopathy (FAC), Senile systemic amyloidosis, and prion disease. There is currently a lack of pharmaceutical agents that disaggregate and/or prevent formation of these unwanted aggregates.

Tramiprosate, 3-amino-1-propanesulfonic acid (SAPS) is an oral amyloid anti-aggregation agent which reduces amyloid beta oligomer neurotoxicity. The tramiprosate Phase 3 trials in mild-to-moderate AD showed an excellent drug profile, including the capability to slow the reduction of brain hippocampal volume, and to improve brain cognition and function in subset analyses. See e.g., Gauthier, S. et al. Effect of tramiprosate in patients with mild-to-moderate Alzheimer's disease: exploratory analyses of the MRI subgroup of the Alphase study. J Nutr Health Aging 13, 550-557 (2009); Saumier, D., Duong, A., Haine, D., Garceau, D. & Sampalis, J. Domain-specific cognitive effects of tramiprosate in patients with mild to moderate Alzheimer's disease: ADAS-cog subscale results from the Alphase Study. J Nutr Health Aging 13, 808-812 (2009); and Aisen, P. S. et al. Tramiprosate in mild-to-moderate Alzheimer's disease—a randomized, double-blind, placebo-controlled, multi-centre study (the Alphase Study). Arch Med Sci 7, 102-111 (2011). More recently, it has been shown that tramiprosate prevents the formation of Aβ42 oligomers, and thus reduces amyloid toxicity, through a novel enveloping mechanism of action.

ALZ-801 (3-(2-amino-3-methylbutanamido)propane-1-sulfonic acid), a new prodrug of 3-amino-1-propanesulfonic acid (SAPS, Tramiprosate) is a promising product which provides more consistent plasma exposures and improved GI tolerability then tramiprosate. ALZ-801 is currently in clinical development for treatment of AD.

Despite the great potential of ALZ-801, the need remains for the use of additional agents for preventing and treating amyloid-related diseases such as Alzheimer's disease.

SUMMARY

Provided herein is the use of a compound of structural formula I:

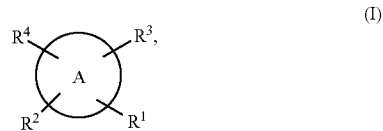

or a pharmaceutically acceptable salt thereof, for treating a disease characterized by amyloid aggregates, wherein the variables A, $R^1$, $R^2$, $R^3$, and $R^4$ are as described herein.

Also provided is the use of a compound of structural formula II:

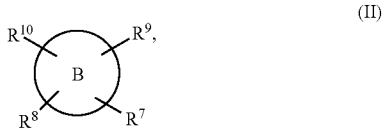

or a pharmaceutically acceptable salt thereof, for treating a disease characterized by amyloid aggregates, wherein the variables B, $R^7$, $R^8$ $R^9$, and $R^{10}$ are as described herein.

Also provided is the use of a compound of structural formula III:

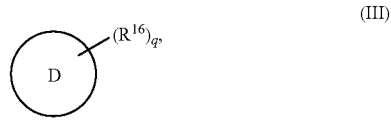

or a pharmaceutically acceptable salt thereof, for treating a disease characterized by amyloid aggregates, wherein the variables D, q, and $R^{16}$ are as described herein.

Also provided is the use of a compound of structural formula IV:

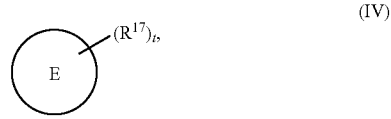

or a pharmaceutically acceptable salt thereof, for treating a disease characterized by amyloid aggregates, wherein the variables E, t, and R$^{17}$ are as described herein.

Further provided is the use of a pharmaceutical composition comprising a compound of structural formula I, II, III, or IV or a pharmaceutically acceptable salt thereof, for treating a disease characterized by amyloid and amyloid-like aggregates (e.g., Alzheimer's disease).

Diseases characterized by amyloid and amyloid-like aggregates include those described herein.

DETAILED DESCRIPTION

1. Definitions

As used herein, a hyphen ("-") at the beginning or end of a recited group designates the point at which a recited group is attached to a defined group. For example, —SO$_2$—(C$_1$-C$_3$)alkyl-(C$_2$-C$_6$)cycloalkyl means that the group is attached via the sulfonyl.

The term "alkylene" refers to a straight or branched bivalent alkyl group.

The term "C$_0$ alkylene" as used herein means a bond. Thus, a moiety defined herein as "—(C$_0$-C$_6$ alkylene)-aryl" includes both-aryl (i.e., C$_0$ alkylene-aryl) and —(C$_1$-C$_6$ alkylene)-aryl.

The term "alkenylene" refers to a straight or branched bivalent alkenyl group.

The term "alkynylene" refers to a straight or branched bivalent alkynyl group.

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl", used alone or as a part of a larger moiety such as e.g., "haloalkenyl", means a monovalent group derived from a straight- or branched-chain aliphatic moiety having at least one carbon-carbon double bond having, unless otherwise specified 1-10 carbon atoms. Representative alkenyl groups include, but are not limited to, ethenyl ("vinyl"), propenyl ("allyl"), butenyl, 1-methyl-2-buten-1-yl, and the like.

The term "alkynyl", used alone or as a part of a larger moiety such as e.g., "haloalkynyl", means a monovalent group derived from a straight- or branched-chain aliphatic moiety having at least one carbon-carbon triple bond having, unless otherwise specified 1-10 carbon atoms. Representative alkynyl groups include, but are not limited to, ethynyl, 2-propynyl ("propargyl"), 1-propynyl, and the like.

The terms "halo" and "halogen" as used herein refer to an atom selected from fluorine (fluoro, —F), chlorine (chloro, —Cl), bromine (bromo, —Br), and iodine (iodo, —I).

The term "carbocyclyl" (also referred to herein as "carbocycle" "cycloaliphatic" or "cycloalkyl"), as used herein, means a monocyclic hydrocarbon or bicyclic hydrocarbon that is completely saturated.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic. The term "aryl" may be used interchangeably with the term "aryl ring". In certain embodiments, "aryl" refers to an aromatic ring system which includes, but not limited to, phenyl, biphenyl, naphthyl, anthracyl and the like. It will be understood that when specified, optional substituents on an aryl group may be present on any substitutable position.

The term "heteroaryl" used alone or as part of a larger moiety as in "heteroarylalkyl", "heteroarylalkoxy", or "heteroarylaminoalkyl", refers to a 5- to 12-membered aromatic radical containing 1-4 heteroatoms selected from N, O, and S. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, and pyrazinyl. Bi-cyclic heteroaryls include groups in which a monocyclic heteroaryl ring is fused to one or more aryl or heteroaryl rings. Nonlimiting examples include indolyl, benzoxazolyl, benzoxodiazolyl, indazolyl, benzimidazolyl, benzthiazolyl, quinolyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached. In one aspect, the term "heteroaryl" also includes ring systems containing a quarternary nitrogen. One example of such a compound is Compound 165, herein:

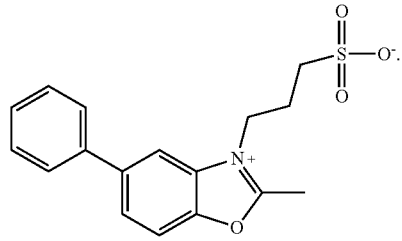

The term "heterocyclyl" means a 4- to 12-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. A heterocyclyl group may be mono- or bicyclic. Examples of monocyclic saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. Bi-cyclic heterocyclyl groups include, e.g., unsaturated heterocyclic radicals fused to another unsaturated heterocyclic radical, cycloalkyl, or aromatic or heteroaryl ring, such as for example, benzodioxolyl, dihydrobenzodioxinyl, 6,7-dihydro-5H-pyrrolo[2,1-c][1,2,4]triazolyl, 5,6,7,8-tetrahydroimidazo[1,2-a]pyridinyl, 1,2-dihydroquinolinyl, dihydrobenzofuranyl, tetrahydronaphthyridine, indolinone, dihydropyrrolotriazole, quinolinone, dioxaspirodecane. It will be understood that when specified, optional substituents on a heterocyclyl group may be present on any substitutable position and, include, e.g., the position at which the heterocyclyl is attached.

The compounds described herein may have chiral centers and/or geometric centers (E- and Z-isomers). It will be understood that the present disclosure encompasses all stereoisomers and geometric isomers. Tautomeric forms of the compounds described herein are also part of the present disclosure.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Example of pharmaceutically acceptable salts are also described, for example, in Berge et al., "Pharmaceutical Salts", J. Pharm. Sci. 66, 1 19 (1977). Such salts include e.g., (1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2 hydroxyethanesulfonic acid, cyclohexylaminosulfonic acid, benzenesulfonic acid, sulfanilic acid, 4-chlorobenzenesulfonic acid, 2 naphthalenesulfonic acid, 4 toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmitiic acid, pantothenic acid, lactobionic acid, alginic acid, galactaric acid, galacturonic acid, gluconic acid, glucoheptonic acid, glutamic acid, naphthoic acid, hydroxynaphthoic acid, salicylic acid, ascorbic acid, stearic acid, muconic acid, and the like; and (2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocaine, procaine, choline, lysine and the like. In one aspect, pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. In one aspect, pharmaceutically acceptable refers to a compound or composition that is approved or approvable by a regulatory agency of the Federal or state government or listed in the U.S. Pharmacopoeia or other generally recognized pharmacopoeia for use in animals and more particularly in humans.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

2. Compounds of the Present Methods

In a first embodiment, provided herein is a method of treating a disease characterized by amyloid aggregates comprising the step of administering to a subject in need thereof a compound of structural formula I:

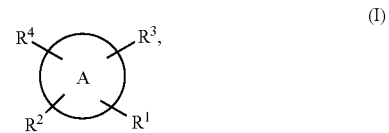

or a pharmaceutically acceptable salt thereof, wherein:
ring A is a 6-membered aryl or a 6-membered heteroaryl comprising 1-3 nitrogen heteroatoms;
$R^1$ is selected from —($C_0$-$C_6$ alkylene)-S(O)$_2$—OH, —($C_2$-$C_6$ alkenylene)-S(O)$_2$—OH, and —($C_2$-$C_6$ alkynylene)-S(O)$_2$—OH;
$R^2$ is selected from hydrogen, —$C_1$-$C_4$ alkyl, —O—$C_1$-$C_4$ alkyl, —($C_0$-$C_6$ alkylene)-N($R^5$)($R^6$), —($C_0$-$C_6$ alkylene)-C(O)—N($R^5$)($R^6$), —($C_0$-$C_6$ alkylene)-C(O)—OH, —($C_0$-$C_6$ alkylene)-C(O)—O—($C_1$-$C_4$ alkyl)-, —($C_2$-$C_6$ alkenylene)-N($R^5$)($R^6$), —($C_2$-$C_6$ alkenylene)-C(O)—N($R^5$)($R^6$), —($C_2$-$C_6$ alkenylene)-C(O)—OH, —($C_2$-$C_6$ alkenylene)-C(O)—O—($C_1$-$C_4$ alkyl), —($C_2$-$C_6$ alkynylene)-N($R^5$)($R^6$), —($C_2$-$C_6$ alkynylene)-C(O)—N($R^5$)($R^6$), —($C_2$-$C_6$ alkynylene)-C(O)—OH, —($C_2$-$C_6$ alkynylene)-C(O)—O—($C_1$-$C_4$ alkyl), —($C_2$-$C_6$ alkenylene)-aryl-N($R^5$)($R^6$), —($C_2$-$C_6$ alkenylene)-aryl-C(O)—N($R^5$)($R^6$), —($C_2$-$C_6$ alkenylene)-aryl-C(O)—OH, —($C_2$-$C_6$ alkynylene)-aryl-N($R^5$)($R^6$), —($C_2$-$C_6$ alkynylene)-aryl-C(O)—N($R^5$)($R^6$), —($C_2$-$C_6$ alkynylene)-aryl-C(O)—OH, —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, —($C_2$-$C_6$ alkenylene)-aryl-S(O)$_2$—OH, —($C_2$-$C_6$ alkynylene)-aryl-S (O)$_2$—OH, —(C$_0$-C$_6$ alkylene)-aryl, —(C$_0$-C$_6$ alkylene)-heteroaryl, —(C$_0$-C$_6$ alkylene)-heterocyclyl, and —(C$_0$-C$_6$ alkylene)-carbocyclyl, wherein up to three methylene units in the C$_0$-C$_6$ alkylene portion of any —(C$_0$-C$_6$ alkylene)-aryl, —(C$_0$-C$_6$ alkylene)-heteroaryl, —(C$_0$-C$_6$ alkylene)-heterocyclyl, or —(C$_0$-C$_6$ alkylene)-carbocyclyl are optionally and independently replaced with —S—, —O—, —NH—, or —N(C$_1$-C$_4$ alkyl)-; and any aryl, heteroaryl, heterocyclyl, or carbocyclyl portion of R$^2$ is optionally substituted with up to 4 substituents independently selected from halo, oxo, —CN, —OH, C$_1$-C$_4$ alkyl, —O—(C$_1$-C$_4$ alkyl), —(C$_0$-C$_6$ alkylene)-N(R$^5$)(R$^6$), —(C$_0$-C$_6$ alkylene)-C(O)—N(R$^5$)(R$^6$), —(C$_0$-C$_6$ alkylene)-C(O)—OH, —(C$_0$-C$_6$ alkylene)-C(O)—O—(C$_1$-C$_4$ alkyl), —(C$_2$-C$_6$ alkenylene)-N(R$^5$)(R$^6$), —(C$_2$-C$_6$ alkenylene)-C(O)—N(R$^5$)(R$^6$), —(C$_2$-C$_6$ alkenylene)-C(O)—OH, —(C$_2$-C$_6$ alkenylene)-C(O)—O—(C$_1$-C$_4$ alkyl), —(C$_2$-C$_6$ alkynylene)-N(R$^5$)(R$^6$), —(C$_2$-C$_6$ alkynylene)-C(O)—N(R$^5$)(R$^6$), —(C$_2$-C$_6$ alkynylene)-C(O)—OH, —(C$_2$-C$_6$ alkynylene)-C(O)—O—(C$_1$-C$_4$ alkyl), —(C$_0$-C$_6$ alkylene)-S(O)$_2$—OH, —(C$_2$-C$_6$ alkenylene)-S(O)$_2$—OH, —(C$_2$-C$_6$ alkynylene)-S(O)$_2$—OH, and —(C$_0$-C$_6$ alkylene)-aryl-S(O)$_2$—OH;

R$^3$ is a substituent bound to a carbon ring atom in ring A and is selected from hydrogen, halogen, —CN, —OH, C$_1$-C$_6$ alkyl, C$_1$-C$_6$ haloalkyl, —(C$_0$-C$_6$ alkylene)-N(R$^5$)(R$^6$), —(C$_0$-C$_6$ alkylene)-C(O)—N(R$^5$)(R$^6$), —(C$_0$-C$_6$ alkylene)-C(O)—OH, —(C$_0$-C$_6$ alkylene)-C(O)—O—(C$_1$-C$_4$ alkyl), —(C$_2$-C$_6$ alkenylene)-N(R$^5$)(R$^6$), —(C$_2$-C$_6$ alkenylene)-C(O)—N(R$^5$)(R$^6$), —(C$_2$-C$_6$ alkenylene)-C(O)—OH, —(C$_2$-C$_6$ alkenylene)-C(O)—O—(C$_1$-C$_4$ alkyl), —(C$_2$-C$_6$ alkynylene)-N(R$^5$)(R$^6$), —(C$_2$-C$_6$ alkynylene)-C(O)—N(R$^5$)(R$^6$), —(C$_2$-C$_6$ alkynylene)-C(O)—OH, —(C$_2$-C$_6$ alkynylene)-C(O)—O—(C$_1$-C$_4$ alkyl), —(C$_0$-C$_6$ alkylene)-aryl-N(R$^5$)(R$^6$), —(C$_0$-C$_6$ alkylene)-aryl-C(O)-aryl-N(R$^5$)(R$^6$), —(C$_0$-C$_6$ alkylene)-aryl-C(O)—OH, —(C$_2$-C$_6$ alkenylene)-aryl-N(R$^5$)(R$^6$), —(C$_2$-C$_6$ alkenylene)-aryl-C(O)—N(R$^5$)(R$^6$), —(C$_2$-C$_6$ alkenylene)-aryl-C(O)—OH, —(C$_2$-C$_6$ alkynylene)-aryl-N(R$^5$)(R$^6$), —(C$_2$-C$_6$ alkynylene)-aryl-C(O)—N(R$^5$)(R$^6$), and —(C$_2$-C$_6$ alkynylene)-aryl-C(O)—OH;

R$^4$ is selected from hydrogen, —OH, C$_1$-C$_4$ alkyl, N(R$^5$)(R$^6$), and phenyl optionally substituted with halogen or hydroxy; and when R$^3$ and R$^4$ are attached to adjacent ring atoms, R$^3$ and R$^4$ are optionally taken together to form a carbocycle, aryl, heterocycle or heteroaryl fused to ring A, wherein the carbocycle, aryl, heterocycle or heteroaryl is optionally substituted with one or more substituents independently selected from halo, oxo, —CN, —OH, C$_1$-C$_4$ alkyl, —O—(C$_1$-C$_4$ alkyl), —(C$_0$-C$_6$ alkylene)-N(R$^5$)(R$^6$), —(C$_0$-C$_6$ alkylene)-C(O)—N(R$^5$)(R$^6$), —(C$_0$-C$_6$ alkylene)-C(O)—OH, —(C$_0$-C$_6$ alkylene)-C(O)—O—(C$_1$-C$_4$ alkyl), —(C$_2$-C$_6$ alkenylene)-N(R$^5$)(R$^6$), —(C$_2$-C$_6$ alkenylene)-C(O)—N(R$^5$)(R$^6$), —(C$_2$-C$_6$ alkenylene)-C(O)—OH, —(C$_2$-C$_6$ alkenylene)-C(O)—O—(C$_1$-C$_4$ alkyl), —(C$_2$-C$_6$ alkynylene)-N(R$^5$)(R$^6$), —(C$_2$-C$_6$ alkynylene)-C(O)—N(R$^5$)(R$^6$), —(C$_2$-C$_6$ alkynylene)-C(O)—OH, —(C$_2$-C$_6$ alkynylene)-C(O)—O—(C$_1$-C$_4$ alkyl), —(C$_0$-C$_6$ alkylene)-S(O)$_2$—OH, —(C$_2$-C$_6$ alkenylene)-S(O)$_2$—OH, —(C$_2$-C$_6$ alkynylene)-S(O)$_2$—OH, and —(C$_0$-C$_6$ alkylene)-aryl, wherein the aryl portion of the substituent is optionally substituted one or two substituents independently selected from —S(O)$_2$—OH and —N(R$^5$)(R$^6$);

each R$^5$ is independently selected from hydrogen, —C(O)—(C$_1$-C$_4$ alkyl), and —C$_1$-C$_4$ alkyl; and each R$^6$ is independently selected from hydrogen, —C$_1$-C$_4$ alkyl, —(C$_0$-C$_4$ alkylene)-carbocycle, —(C$_0$-C$_4$ alkylene)-aryl, —(C$_0$-C$_4$ alkylene)⁻ heterocycle, and —(C$_0$-C$_4$ alkylene)-heteroaryl, and wherein the carbocyclyl, aryl, heteroaryl, or heterocyclyl portion of R$^6$ may be further substituted with up to 4 substituents independently selected from halogen, —CN, —OH, —COOH, —CONH$_2$, and C$_1$-C$_3$ alkyl; or R$^5$ and R$^6$ together form a heterocyclic or heteroaromatic ring optionally substituted with one or more groups selected from halogen, oxo, —NH$_2$, —NH(C$_1$-C$_4$ alkyl), —N(C$_1$-C$_4$ alkyl)$_2$, —CN, —OH, —COOH, —CONH$_2$, and C$_1$-C$_3$ alkyl;

provided the compound comprises no more than two —S(O)$_2$—OH moieties.

In a second embodiment, provided herein is a method of treating a disease characterized by amyloid aggregates comprising the step of administering to a subject in need thereof a compound of structural formula Ia:

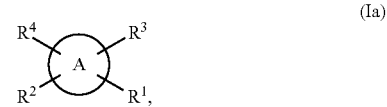

(Ia)

or a pharmaceutically acceptable salt thereof, wherein:

ring A is a 6-membered aryl or heteroaryl comprising 1-3 nitrogen heteroatoms;

R$^1$ is selected from —(C$_0$-C$_6$ alkylene)-S(O)$_2$—OH, —(C$_2$-C$_6$ alkenylene)-S(O)$_2$—OH, and —(C$_2$-C$_6$ alkynylene)-S(O)$_2$—OH;

R$^2$ is selected from hydrogen, —(C$_0$-C$_6$ alkylene)-N(R$^5$)(R$^6$), —(C$_0$-C$_6$ alkylene)-C(O)—N(R$^5$)(R$^6$), —(C$_0$-C$_6$ alkylene)-C(O)—OH, —(C$_2$-C$_6$ alkenylene)-N(R$^5$)(R$^6$), —(C$_2$-C$_6$ alkenylene)-C(O)—N(R$^5$)(R$^6$), —(C$_2$-C$_6$ alkenylene)-C(O)—OH, —(C$_2$-C$_6$ alkynylene)-N(R$^5$)(R$^6$), —(C$_2$-C$_6$ alkynylene)-C(O)—N(R$^5$)(R$^6$), —(C$_2$-C$_6$ alkynylene)-C(O)—OH, —(C$_0$-C$_6$ alkylene)-aryl-N(R$^5$)(R$^6$), —(C$_0$-C$_6$ alkylene)-aryl-C(O)-aryl-N(R$^5$)(R$^6$), —(C$_0$-C$_6$ alkylene)-aryl-C(O)—OH, —(C$_2$-C$_6$ alkenylene)-aryl-N(R$^5$)(R$^6$), —(C$_2$-C$_6$ alkenylene)-aryl-C(O)—N(R$^5$)(R$^6$), —(C$_2$-C$_6$ alkenylene)-aryl-C(O)—OH, —(C$_2$-C$_6$ alkynylene)-aryl-N(R$^5$)(R$^6$), —(C$_2$-C$_6$ alkynylene)-aryl-C(O)—N(R$^5$)(R$^6$), —(C$_2$-C$_6$ alkynylene)-aryl-C(O)—OH, —(C$_0$-C$_6$ alkylene)-S(O)$_2$—OH, —(C$_2$-C$_6$ alkenylene)-S(O)$_2$—OH, —(C$_2$-C$_6$ alkynylene)-S(O)$_2$—OH, —(C$_0$-C$_6$ alkylene)-aryl-S(O)$_2$—OH, —(C$_2$-C$_6$ alkenylene)-aryl-S(O)$_2$—OH, and —(C$_2$-C$_6$ alkynylene)-aryl-S(O)$_2$—OH;

R$^3$ is a substituent bound to a carbon ring atom in ring A and is selected from hydrogen, halogen, —CN, —OH, C$_1$-C$_6$ alkyl, C$_1$-C$_6$ haloalkyl, —(C$_0$-C$_6$ alkylene)-N(R$^5$)(R$^6$), —(C$_0$-C$_6$ alkylene)-C(O)—N(R$^5$)(R$^6$), —(C$_0$-C$_6$ alkylene)-C(O)—OH, —(C$_2$-C$_6$ alkenylene)-N(R$^5$)(R$^6$), —(C$_2$-C$_6$ alkenylene)-C(O)—N(R$^5$)(R$^6$), —(C$_2$-C$_6$ alkenylene)-C(O)—OH, —(C$_2$-C$_6$ alkynylene)-N(R$^5$)(R$^6$), —(C$_2$-C$_6$ alkynylene)-C(O)—N(R$^5$)(R$^6$), —(C$_2$-C$_6$ alkynylene)-C(O)—OH, —(C$_0$-C$_6$ alkylene)-aryl-N(R$^5$)(R$^6$), —(C$_0$-C$_6$ alkylene)-aryl-C(O)-aryl-N(R$^5$)(R$^6$), —(C$_0$-C$_6$ alkylene)-aryl-C(O)—OH, —(C$_2$-C$_6$ alkenylene)-aryl-N(R$^5$)(R$^6$), —(C$_2$-C$_6$ alkenylene)-aryl-C(O)—N(R$^5$)(R$^6$), —(C$_2$-C$_6$ alkenylene)-aryl-C(O)—OH, —(C$_2$-C$_6$ alkynylene)-aryl-N(R$^5$)(R$^6$), —(C$_2$-C$_6$ alkynylene)-aryl-C(O)—N(R$^5$)(R$^6$), and —(C$_2$-C$_6$ alkynylene)-aryl-C(O)—OH;

R$^4$ is hydrogen and when R$^3$ is hydrogen or C$_1$-C$_3$ alkyl, R$^4$ is additionally selected from C$_1$-C$_3$ alkyl and phenyl optionally substituted with halogen or hydroxy; and when R$^3$ and R$^4$ are attached to adjacent ring atoms, R$^3$ and R$^4$ are optionally taken together to form a carbocycle, aryl, heterocycle or heteroaryl fused to ring A, wherein the carbocycle, aryl, heterocycle or heteroaryl is optionally substituted with one or more substituent selected from halo, —CN, —OH, —($C_0$-$C_6$ alkylene)-N($R^5$)($R^6$), —($C_0$-$C_6$ alkylene)-C(O)—N($R^5$)($R^6$), —($C_0$-$C_6$ alkylene)-C(O)—OH, —($C_2$-$C_6$ alkenylene)-N($R^5$)($R^6$), —($C_2$-$C_6$ alkenylene)-C(O)—N($R^5$)($R^6$), —($C_2$-$C_6$ alkenylene)-C(O)—OH, —($C_2$-$C_6$ alkynylene)-N($R^5$)($R^6$), —($C_2$-$C_6$ alkynylene)-C(O)—N($R^5$)($R^6$), —($C_2$-$C_6$ alkynylene)-C(O)—OH, —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, and —($C_0$-$C_6$ alkylene)-aryl-S(O)$_2$—OH;

each $R^5$ is independently selected from hydrogen, —C(O)—($C_1$-$C_4$ alkyl), and —$C_1$-$C_4$ alkyl; and each $R^6$ is independently selected from hydrogen, —$C_1$-$C_4$ alkyl, —($C_0$-$C_4$ alkylene)-carbocycle, —($C_0$-$C_4$ alkylene)-aryl, —($C_0$-$C_4$ alkylene)-heterocycle, —($C_0$-$C_4$ alkylene)-heteroaryl, and wherein the carbocyclyl, aryl, heteroaryl, or heterocyclyl portion of $R^6$ may be further substituted with up to 4 substituents independently selected from halogen, —CN, —OH, —COOH, —CONH$_2$, and $C_1$-$C_3$ alkyl; or $R^5$ and $R^6$ together form a heterocyclic or heteroaromatic ring optionally substituted with one or more groups selected from halogen, —CN, —OH, —COOH, —CONH$_2$, and $C_1$-$C_3$ alkyl;

provided the compound comprises no more than two —S(O)$_2$—OH moieties.

In a third embodiment of the methods described herein, $R^1$ in structural formula I or Ia is selected from —S(O)$_2$—OH and —CH$_2$—S(O)$_2$—OH, wherein the remaining variables are as described above for structural formula I or Ia. Alternatively, $R^1$ in structural formula I or Ia is bound to a ring carbon and selected from —S(O)$_2$—OH and —CH$_2$—S(O)$_2$—OH, wherein the remaining variables are as described above for structural formula I or Ia. In another alternative, $R^1$ in structural formula I or Ia is bound to a ring carbon and is —S(O)$_2$—OH, wherein the remaining variables are as described above for structural formula I or Ia.

In a fourth embodiment of the methods described herein, $R^2$ in structural formula I or Ia is selected from —NH$_2$, —CH$_2$NH$_2$, —C(O)NH$_2$, and —COOH, wherein the remaining variables are as described above for structural formula I or Ia, or the third embodiment thereof. Alternatively, $R^2$ in structural formula I or Ia is bound to a ring carbon and selected from —CH$_2$NH$_2$, —CH$_2$COOH, and —CH$_2$C(O)NH$_2$, wherein the remaining variables are as described above for structural formula I or Ia, or third embodiment thereof. In another alternative, $R^2$ in structural formula I or Ia is bound to a ring carbon and is —NH$_2$, wherein the remaining variables are as described above for structural formula I or Ia, or third embodiment thereof.

In a fifth embodiment of the methods described herein, ring A in structural formula I or Ia is phenyl, wherein the remaining variables are as described above for structural formula I or Ia, or the third or fourth embodiment thereof described above. In other aspects of the first embodiment of the methods described herein, ring A in structural formula I or Ia is selected from pyridine, pyrimidine, pyrazine, pyridazine, and triazine, wherein the remaining variables are as described above for structural formula I or Ia, or the third or fourth embodiment thereof In a sixth embodiment, provided herein is a method of treating a disease characterized by amyloid aggregates comprising the step of administering to a subject in need thereof a compound of structural formula I-1,

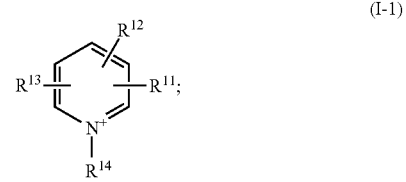

(I-1)

or a pharmaceutically acceptable salt thereof, wherein:
$R^{11}$ is —($C_0$-$C_4$ alkylene)-SO$_3^-$;
$R^{12}$ is selected from hydrogen, —($C_0$-$C_4$ alkylene)-aryl, —($C_0$-$C_4$ alkylene)-heteroaryl, —($C_0$-$C_4$ alkylene)-carbocyclyl, and —($C_0$-$C_4$ alkylene)-heterocyclyl
$R^{13}$ is selected from hydrogen, $C_1$-$C_6$ alkyl, ($C_0$-$C_6$ alkylene)-NH$_2$, and ($C_0$-$C_6$ alkylene)-C(O)—NH$_2$; and
$R^{14}$ is $C_1$-$C_4$ alkyl.

In a seventh embodiment, provided herein is a method of treating a disease characterized by amyloid aggregates comprising the step of administering to a subject in need thereof a compound of structural formula I, wherein $R^3$ and $R^4$ are taken together with ring A to form a bicyclic ring quaternary nitrogen-containing ring system, wherein the remaining variables are as described above for structural formula I or Ia or the third, fourth, or fifth embodiment thereof described above. In one aspect of the seventh embodiment, $R^3$ and $R^4$ are taken together with ring A to form a bicyclic ring system comprising one quaternary nitrogen, wherein the remaining variables are as described above for structural formula I or Ia or the third, fourth, or fifth embodiment thereof described above. In some aspects of the seventh embodiment, the quaternary nitrogen is a ring atom in the ring A portion of the bicyclic ring system, wherein the remaining variables are as described above for structural formula I or Ia. In some aspects of the seventh embodiment, the quaternary nitrogen is a bridgehead atom in the bicyclic ring system, wherein the remaining variables are as described above for structural formula I or Ia or the third, fourth, or fifth embodiment thereof described above. In some aspects of the seventh embodiment, the quaternary nitrogen is a ring atom in the portion of the bicyclic ring system formed by taking $R^3$ and $R^4$ together, wherein the remaining variables are as described above for structural formula I or Ia or the third, fourth, or fifth embodiment thereof described above. In some aspects of the seventh embodiment, the quaternary nitrogen, when substitutable, is substituted with $R^4$, wherein the remaining variables are as described above for structural formula I or Ia or the third, fourth, or fifth embodiment thereof described above. In some aspects of the seventh embodiment, the quaternary nitrogen, when substitutable, is substituted with a $C_1$-$C_4$ alkyl, wherein the remaining variables are as described above for structural formula I or Ia or the third, fourth, or fifth embodiment thereof described above. In some aspects of the seventh embodiment, the compound of structural formula I has the formula:

Ib

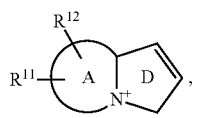

(Ib)

-continued (Ic)

[Structure Ic: R^11—(A ring)—R^12, fused to ring C with N^+]

(Id)

[Structure Id: R^11—(A ring)—R^12, fused through D to N^+—R^15, and]

(Ie)

[Structure Ie: R^11—(A ring)—R^12, fused to ring C with N^+—R^15]

or a pharmaceutically acceptable salt thereof, wherein:

ring C is a ring formed by taking together $R^3$ and $R^4$, wherein ring C optionally comprises 1 to 2 ring nitrogen atoms in addition to the quaternary nitrogen;

ring D is a ring formed by taking together $R^3$ and $R^4$, wherein ring D optionally comprises 1 to 2 ring heteroatoms selected from S, O and N in addition to the quaternary nitrogen;

$R^{11}$ is —($C_0$-$C_4$ alkylene)-$SO_3^-$;

$R^{12}$ is selected from hydrogen, —($C_0$-$C_4$ alkylene)-aryl, —($C_0$-$C_4$ alkylene)-heteroaryl, —($C_0$-$C_4$ alkylene)-carbocyclyl, and —($C_0$-$C_4$ alkylene)-heterocyclyl; and $R^{15}$ is $C_1$-$C_4$ alkyl.

In an eighth embodiment, provided herein is a method of treating a disease characterized by amyloid aggregates comprising the step of administering to a subject in need thereof a compound of structural formula I or Ia, or a pharmaceutical salt thereof, wherein:

ring A is selected from pyridine and pyrimidine;

$R^1$ is selected from —($C_0$-$C_4$ alkylene)-S(O)$_2$—OH, —($C_2$-$C_4$ alkenylene)-S(O)$_2$—OH, and —($C_2$-$C_4$ alkynylene)-S(O)$_2$—OH;

$R^2$ is selected from —($C_0$-$C_6$ alkylene)-NH$_2$, —($C_2$-$C_4$ alkenylene)-NH$_2$, and —($C_2$-$C_4$ alkynylene)-NH$_2$;

$R^3$ is selected from hydrogen and $C_1$-$C_6$ alkyl; and $R^4$ is hydrogen.

In a ninth embodiment, provided herein is a method of treating a disease characterized by amyloid aggregates comprising the step of administering to a subject in need thereof a compound of structural formula I or Ia, wherein $R^1$ is —S(O)$_2$—OH; and $R^2$ is —NH$_2$; and wherein the remaining variables are as described above for structural formula I or Ia or the third, fourth, fifth, or eighth embodiment thereof described above.

In a tenth embodiment, provided herein is a method of treating a disease characterized by amyloid aggregates comprising the step of administering to a subject in need thereof a compound of structural formula I or Ia, wherein ring A comprises a quaternary nitrogen ring atom substituted with $C_1$-$C_4$ alkyl; and $R^1$ is —SO$_3^-$; and wherein the remaining variables are as described above for structural formula I or Ia or the third, fourth, fifth, eighth, or ninth embodiment thereof described above.

In an eleventh embodiment, provided herein is a method of treating a disease characterized by amyloid aggregates comprising the step of administering to a subject in need thereof a compound of structural formula I or Ia, wherein $R^1$ is —SO$_3^-$; and $R^2$ is selected from heteroaryl and heterocyclyl; and $R^2$ comprises a quaternary nitrogen ring atom; and wherein the remaining variables are as described above for structural formula I or Ia or the third, fourth, fifth, eighth, ninth, or tenth embodiment thereof described above.

In a twelfth embodiment, provided herein is a method of treating a disease characterized by amyloid aggregates comprising the step of administering to a subject in need thereof a compound of structural formula II:

(II)

[Structure II: ring B with substituents $R^{10}$, $R^9$, $R^8$, $R^7$]

or pharmaceutically acceptable salt thereof, wherein:

ring B is a 5-membered heteroaromatic ring comprising 1-3 heteroatoms, wherein:

the first heteroatom is N, or S or S(O)$_2$;

the second heteroatom, if present, is N or O, wherein when the first heteroatom is S or S(O)$_2$, the second heteroatom is N; and the third heteroatom, if present, is N;

$R^7$ is selected from —($C_0$-$C_6$ alkylene)-S(O)$_2$—OH, —($C_2$-$C_6$ alkenylene)-S(O)$_2$—OH, and —($C_2$-$C_6$ alkynylene)-S(O)$_2$—OH;

$R^8$ is selected from hydrogen, —$C_1$-$C_4$ alkyl, —O—$C_1$-$C_4$ alkyl, —($C_0$-$C_6$ alkylene)-N($R^{10}$)($R^{11}$), —($C_0$-$C_6$ alkylene)-C(O)—N($R^{10}$)($R^{11}$), —($C_0$-$C_6$ alkylene)-C(O)—OH, —($C_0$-$C_6$ alkylene)-C(O)—O—($C_1$-$C_4$ alkyl)-, —($C_2$-$C_6$ alkenylene)-N($R^{10}$)($R^{11}$), —($C_2$-$C_6$ alkenylene)-C(O)—N($R^{10}$)($R^{11}$), —($C_2$-$C_6$ alkenylene)-C(O)—OH, —($C_2$-$C_6$ alkenylene)-C(O)—O—($C_1$-$C_4$ alkyl), —($C_2$-$C_6$ alkynylene)-N($R^{10}$)($R^{11}$), —($C_2$-$C_6$ alkynylene)-C(O)—N($R^{10}$)($R^{11}$), —($C_2$-$C_6$ alkynylene)-C(O)—OH, —($C_2$-$C_6$ alkynylene)-C(O)—O—($C_1$-$C_4$ alkyl), —($C_2$-$C_6$ alkenylene)-aryl-N($R^{10}$)($R^{11}$), —($C_2$-$C_6$ alkenylene)-aryl-C(O)—N($R^{10}$)($R^{11}$), —($C_2$-$C_6$ alkenylene)-aryl-C(O)—OH, —($C_2$-$C_6$ alkynylene)-aryl-N($R^{10}$)($R^{11}$), —($C_2$-$C_6$ alkynylene)-aryl-C(O)—N($R^{10}$)($R^{11}$), —($C_2$-$C_6$ alkynylene)-aryl-C(O)—OH, —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, —($C_2$-$C_6$ alkenylene)-aryl-S(O)$_2$—OH, —($C_2$-$C_6$ alkynylene)-aryl-S(O)$_2$—OH, —($C_0$-$C_6$ alkylene)-aryl, —($C_0$-$C_6$ alkylene)-heteroaryl, —($C_0$-$C_6$ alkylene)-heterocyclyl, and —($C_0$-$C_6$ alkylene)-carbocyclyl, wherein up to three methylene units in the $C_0$-$C_6$ alkylene portion of any —($C_0$-$C_6$ alkylene)-aryl, —($C_0$-$C_6$ alkylene)-heteroaryl, —($C_0$-$C_6$ alkylene)-heterocyclyl, or —($C_0$-$C_6$ alkylene)-carbocyclyl are optionally and independently replaced with —S—, —O—, —NH—, or —N($C_1$-$C_4$ alkyl)-; and any aryl, heteroaryl, heterocyclyl, or carbocyclyl portion of $R^2$ is optionally substituted with up to 4 substituents independently selected from halo, oxo, —CN, —OH, $C_1$-$C_4$ alkyl, —O—($C_1$-$C_4$ alkyl), —($C_0$-$C_6$ alkylene)-N($R^{10}$)($R^{11}$), —($C_0$-$C_6$ alkylene)-C(O)—N($R^{10}$)($R^{11}$), —($C_0$-$C_6$ alkylene)-C(O)—OH, —($C_0$-$C_6$ alkylene)-C(O)—O—($C_1$-$C_4$ alkyl), —($C_2$-$C_6$ alkenylene)-N($R^{10}$)($R^{11}$), —($C_2$-$C_6$ alkenylene)-C(O)—N($R^{10}$)($R^{11}$), —($C_2$-$C_6$ alkenylene)-C(O)—OH, —($C_2$-$C_6$ alkenylene)-C(O)—O—($C_1$-$C_4$ alkyl), —($C_2$-$C_6$ alkynylene)-N($R^{10}$)($R^{11}$), —($C_2$-$C_6$ alkynylene)-C(O)—N($R^{10}$)

($R^{11}$), —($C_2$-$C_6$ alkynylene)-C(O)—OH, —($C_2$-$C_6$ alkynylene)-C(O)—O—($C_1$-$C_4$ alkyl), —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, and —($C_0$-$C_6$ alkylene)-aryl-S(O)$_2$—OH;

$R^9$ is a substituent bound to a carbon ring atom in ring B and is selected from hydrogen, halogen, —CN, —OH, $C_1$-$C_6$ alkyl, $C_1$-$C_6$ haloalkyl, —($C_0$-$C_6$ alkylene)-N($R^{10}$)($R^{11}$), —($C_0$-$C_6$ alkylene)-C(O)—N($R^{10}$)($R^{11}$), —($C_0$-$C_6$ alkylene)-C(O)—OH, —($C_0$-$C_6$ alkylene)-C(O)—O—($C_1$-$C_4$ alkyl), —($C_2$-$C_6$ alkenylene)-N($R^{10}$)($R^{11}$), —($C_2$-$C_6$ alkenylene)-C(O)—N($R^{10}$)($R^{11}$), —($C_2$-$C_6$ alkenylene)-C(O)—OH, —($C_2$-$C_6$ alkenylene)-C(O)—O—($C_1$-$C_4$ alkyl), —($C_2$-$C_6$ alkynylene)-N($R^{10}$)($R^{11}$), —($C_2$-$C_6$ alkynylene)-C(O)—N($R^{10}$)($R^{11}$), —($C_2$-$C_6$ alkynylene)-C(O)—OH, —($C_2$-$C_6$ alkynylene)-C(O)—O—($C_1$-$C_4$ alkyl), —($C_0$-$C_6$ alkylene)-aryl-N($R^{10}$)($R^{11}$), —($C_0$-$C_6$ alkylene)-aryl-C(O)-aryl-N($R^{10}$)($R^{11}$), —($C_0$-$C_6$ alkylene)-aryl-C(O)—OH, —($C_2$-$C_6$ alkenylene)-aryl-N($R^{10}$)($R^{11}$), —($C_2$-$C_6$ alkenylene)-aryl-C(O)—N($R^{10}$)($R^{11}$), —($C_2$-$C_6$ alkenylene)-aryl-C(O)—OH, —($C_2$-$C_6$ alkynylene)-aryl-N($R^{10}$)($R^{11}$), —($C_2$-$C_6$ alkynylene)-aryl-C(O)—N($R^{10}$)($R^{11}$), and —($C_2$-$C_6$ alkynylene)-aryl-C(O)—OH;

$R^{10}$ is selected from hydrogen, —OH, $C_1$-$C_4$ alkyl, N($R^{10}$)($R^{11}$), and phenyl optionally substituted with halogen or hydroxy; and when $R^9$ and $R^{10}$ are attached to adjacent ring atoms, $R^9$ and $R^{10}$ are optionally taken together to form a carbocycle, aryl, heterocycle or heteroaryl fused to ring A, wherein the carbocycle, aryl, heterocycle or heteroaryl is optionally substituted with one or more substituents independently selected from halo, oxo, —CN, —OH, $C_1$-$C_4$ alkyl, —O—($C_1$-$C_4$ alkyl), —($C_0$-$C_6$ alkylene)-N($R^{11}$)($R^{12}$), —($C_0$-$C_6$ alkylene)-C(O)—N($R^{11}$)($R^{12}$), —($C_0$-$C_6$ alkylene)-C(O)—OH, —($C_0$-$C_6$ alkylene)-C(O)—O—($C_1$-$C_4$ alkyl), —($C_2$-$C_6$ alkenylene)-N($R^{11}$)($R^{12}$), —($C_2$-$C_6$ alkenylene)-C(O)—N($R^{10}$)($R^{11}$), —($C_2$-$C_6$ alkenylene)-C(O)—OH, —($C_2$-$C_6$ alkenylene)-C(O)—O—($C_1$-$C_4$ alkyl), —($C_2$-$C_6$ alkynylene)-N($R^{10}$)($R^{11}$), —($C_2$-$C_6$ alkynylene)-C(O)—N($R^{10}$)($R^{11}$), —($C_2$-$C_6$ alkynylene)-C(O)—OH, —($C_2$-$C_6$ alkynylene)-C(O)—O—($C_1$-$C_4$ alkyl), —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, and —($C_0$-$C_6$ alkylene)-aryl, wherein the aryl portion of the substituent is optionally substituted one or two substituents independently selected from —S(O)$_2$—OH and —N($R^{10}$)($R^{11}$);

each $R^{11}$ is independently selected from hydrogen, —C(O)—($C_1$-$C_4$ alkyl), and —$C_1$-$C_4$ alkyl; each $R^{12}$ is independently selected from hydrogen, —$C_1$-$C_4$ alkyl, —($C_0$-$C_4$ alkylene)-carbocycle, —($C_0$-$C_4$ alkylene)-aryl, —($C_0$-$C_4$ alkylene)-heterocycle, and —($C_0$-$C_4$ alkylene)-heteroaryl, and wherein the carbocyclyl, aryl, heteroaryl, or heterocyclyl portion of $R^{12}$ may be further substituted with up to 4 substituents independently selected from halogen, —CN, —OH, —COOH, —CONH$_2$, and $C_1$-$C_3$ alkyl; or $R^{11}$ and $R^{12}$ together form a heterocyclic or heteroaromatic ring optionally substituted with one or more groups selected from halogen, oxo, —NH$_2$, —NH($C_1$-$C_4$ alkyl), —N($C_1$-$C_4$ alkyl)$_2$, —CN, —OH, —COOH, —CONH$_2$, and $C_1$-$C_3$ alkyl;

provided the compound comprises no more than two —S(O)$_2$—OH moieties.

In a thirteenth embodiment, provided herein is a method of treating a disease characterized by amyloid aggregates comprising the step of administering to a subject in need thereof a compound of structural formula IIa:

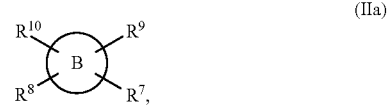

(IIa)

or a pharmaceutically acceptable salt thereof, wherein:

ring B is a 5-membered heteroaromatic ring comprising 1-3 heteroatoms, wherein:
 the first heteroatom is N, or S or S(O)$_2$;
 the second heteroatom, if present, is N or O, wherein when the first heteroatom is S or S(O)$_2$, the second heteroatom is N; and
 the third heteroatom, if present, is N;

$R^7$ is selected from —($C_0$-$C_6$ alkylene)-S(O)$_2$—OH, —($C_2$-$C_6$ alkenylene)-S(O)$_2$—OH, and —($C_2$-$C_6$ alkynylene)-S(O)$_2$—OH;

$R^8$ is selected from —($C_0$-$C_6$ alkylene)-N($R^{11}$)($R^{12}$), —($C_0$-$C_6$ alkylene)-C(O)—N($R^{11}$)($R^{12}$), —($C_0$-$C_6$ alkylene)-C(O)—OH, —($C_2$-$C_6$ alkenylene)-N($R^{11}$)($R^{12}$), —($C_2$-$C_6$ alkenylene)-C(O)—N($R^{11}$)($R^{12}$), —($C_2$-$C_6$ alkenylene)-C(O)—OH, —($C_2$-$C_6$ alkynylene)-N($R^{11}$)($R^{12}$), —($C_2$-$C_6$ alkynylene)-C(O)—N($R^{11}$)($R^{12}$), —($C_2$-$C_6$ alkynylene)-C(O)—OH, —($C_0$-$C_6$ alkylene)-aryl-N($R^{11}$)($R^{12}$), —($C_0$-$C_6$ alkylene)-aryl-C(O)-aryl-N($R^{11}$)($R^{12}$), —($C_0$-$C_6$ alkylene)-aryl-C(O)—OH, —($C_2$-$C_6$ alkenylene)-aryl-N($R^{11}$)($R^{12}$), —($C_2$-$C_6$ alkenylene)-aryl-C(O)—N($R^{11}$)($R^{12}$), —($C_2$-$C_6$ alkenylene)-aryl-C(O)—OH, —($C_2$-$C_6$ alkynylene)-aryl-N($R^{11}$)($R^{12}$), —($C_2$-$C_6$ alkynylene)-aryl-C(O)—N($R^{11}$)($R^{12}$), —($C_2$-$C_6$ alkynylene)-aryl-C(O)—OH, —($C_0$-$C_6$ alkylene)-S(O)$_2$—OH, —($C_2$-$C_6$ alkenylene)-S(O)$_2$—OH, —($C_2$-$C_6$ alkynylene)-S(O)$_2$—OH, —($C_0$-$C_6$ alkylene)-aryl-S(O)$_2$—OH, —($C_2$-$C_6$ alkenylene)-aryl-S(O)$_2$—OH, and —($C_2$-$C_6$ alkynylene)-aryl-S(O)$_2$—OH;

$R^9$ is a substituent bound to a carbon ring atom in ring B and is selected from hydrogen, halogen, —CN, —OH, $C_1$-$C_6$ alkyl, $C_1$-$C_6$ haloalkyl, —($C_0$-$C_6$ alkylene)-N($R^{11}$)($R^{12}$), —($C_0$-$C_6$ alkylene)-C(O)—N($R^{11}$)($R^{12}$), —($C_0$-$C_6$ alkylene)-C(O)—OH, —($C_2$-$C_6$ alkenylene)-N($R^{11}$)($R^{12}$), —($C_2$-$C_6$ alkenylene)-C(O)—N($R^{11}$)($R^{12}$), —($C_2$-$C_6$ alkenylene)-C(O)—OH, —($C_2$-$C_6$ alkynylene)-N($R^{11}$)($R^{12}$), —($C_2$-$C_6$ alkynylene)-C(O)—N($R^{11}$)($R^{12}$), —($C_2$-$C_6$ alkynylene)-C(O)—OH, —($C_0$-$C_6$ alkylene)-aryl-N($R^{11}$)($R^{12}$), —($C_0$-$C_6$ alkylene)-aryl-C(O)-aryl-N($R^{11}$)($R^{12}$), —($C_0$-$C_6$ alkylene)-aryl-C(O)—OH, —($C_2$-$C_6$ alkenylene)-aryl-N($R^{11}$)($R^{12}$), —($C_2$-$C_6$ alkenylene)-aryl-C(O)—N($R^{11}$)($R^{12}$), —($C_2$-$C_6$ alkenylene)-aryl-C(O)—OH, —($C_2$-$C_6$ alkynylene)-aryl-N($R^{11}$)($R^{12}$), —($C_2$-$C_6$ alkynylene)-aryl-C(O)—N($R^{11}$)($R^{12}$), and —($C_2$-$C_6$ alkynylene)-aryl-C(O)—OH;

$R^{10}$ is hydrogen and when $R^9$ is hydrogen or $C_1$-$C_3$ alkyl, $R^{10}$ is additionally selected from $C_1$-$C_3$ alkyl and phenyl optionally substituted with halogen or hydroxy; and when $R^9$ and $R^{10}$ are attached to adjacent ring atoms, $R^9$ and $R^{10}$ are optionally taken together to form a carbocycle, aryl, heterocycle or heteroaryl fused to ring A, wherein the carbocycle, aryl, heterocycle or heteroaryl is optionally substituted with one or more substituent selected from halo, —CN, —OH, —($C_0$-$C_6$ alkylene)-N($R^{11}$)($R^{12}$), —($C_0$-$C_6$ alkylene)-C(O)—N($R^{11}$)($R^{12}$), —($C_0$-$C_6$ alkylene)-C(O)—OH, —($C_2$-$C_6$ alkenylene)-N($R^{11}$)($R^{12}$), —($C_2$-$C_6$ alkenylene)-C(O)—N($R^{11}$)($R^{12}$), —($C_2$-$C_6$ alkenylene)-C(O)—OH, —($C_2$-$C_6$ alkynylene)-N($R^{11}$)($R^{12}$), —($C_2$-$C_6$ alkynylene)-C(O)—N($R^{11}$)($R^{12}$), —($C_2$-$C_6$ alkynylene)-C(O)—OH, —($C_0$-$C_6$ alkylene)-S(O)$_2$—OH, —($C_2$-$C_6$ alkenylene)-S(O)$_2$—OH, —(C$_2$-C$_6$ alkynylene)-S(O)$_2$—OH, and —(C$_0$-C$_6$ alkylene)-aryl-S(O)$_2$—OH;

each $R^{11}$ is independently selected from hydrogen, —C(O)—(C$_1$-C$_4$ alkyl), and —C$_1$-C$_4$ alkyl;

each $R^{12}$ is independently selected from hydrogen, —C$_1$-C$_4$ alkyl, —(C$_0$-C$_4$ alkylene)-carbocycle, —(C$_0$-C$_4$ alkylene)-aryl, —(C$_0$-C$_4$ alkylene)-heterocycle, —(C$_0$-C$_4$ alkylene)-heteroaryl, and wherein the carbocyclyl, aryl, heteroaryl, or heterocyclyl portion of $R^{12}$ may be further substituted with up to 4 substituents independently selected from halogen, —CN, —OH, —COOH, —CONH$_2$, and C$_1$-C$_3$ alkyl; or $R^{11}$ and $R^{12}$ together form a heterocyclic or heteroaromatic ring optionally substituted with one or more groups selected from halogen, —CN, —OH, —COOH, —CONH$_2$, and C$_1$-C$_3$ alkyl;

provided the compound comprises no more than two —S(O)$_2$—OH moieties.

In a fourteenth embodiment of the methods described herein, $R^7$ in structural formula II or IIa is selected from —S(O)$_2$—OH and —CH$_2$—S(O)$_2$—OH, wherein the remaining variables are as described above for structural formula II or IIa.

In a fifteenth embodiment of the methods described herein, $R^8$ in structural formula II or IIa is attached to a ring carbon and is selected from —NH$_2$, —CH$_2$NH$_2$, —C(O)NH$_2$, and —COOH, wherein the remaining variables are as described above for structural formula II or IIa, or the fourteenth embodiment thereof. In some aspects of the fifteenth embodiment, $R^8$ in structural formula II or IIa is attached to a ring nitrogen and is selected from —CH$_2$NH$_2$, —CH$_2$C(O)NH$_2$, and —CH$_2$COOH, wherein the remaining variables are as described above for structural formula II or IIa, or the fourteenth embodiment thereof.

In a sixteenth embodiment of the methods described herein, ring B in structural formula II or IIa is selected from pyrrole, pyrazole, imidazole, triazole, thiophene, thiadiazole, and thiazole, wherein the remaining variables are as described above for structural formula II or IIa, or the fourteenth or fifteenth embodiment thereof.

In a seventeenth embodiment, provided herein is a method of treating a disease characterized by amyloid aggregates comprising the step of administering to a subject in need thereof a compound of structural formula II or IIa, wherein $R^9$ and $R^{10}$ are taken together with ring B to form a bicyclic, quaternary nitrogen-containing ring system, wherein the remaining variables are as described above for structural formula II or IIa. In some aspects of the seventeenth embodiment, the quaternary nitrogen is a ring atom in the ring B portion of the bicyclic ring system, wherein the remaining variables are as described above for structural formula II or IIa. In some aspects of the seventeenth embodiment, the quaternary nitrogen is a bridgehead atom in the bicyclic ring system, wherein the remaining variables are as described above for structural formula II or IIa. In some aspects of the seventeenth embodiment, the quaternary nitrogen is a ring atom in the portion of the bicyclic ring system formed by taking $R^9$ and $R^{10}$ together, wherein the remaining variables are as described above for structural formula II or IIa. In some aspects of the seventeenth embodiment, the quaternary nitrogen, when substitutable, is substituted with $R^{10}$, wherein the remaining variables are as described above for structural formula II or IIa. In more specific aspects of the seventeenth embodiment, the quaternary nitrogen, when substitutable, is substituted with a C$_1$-C$_4$ alkyl, wherein the remaining variables are as described above for structural formula II or IIa. In still further specific aspects of the seventeenth embodiment, the compound of structural formula II has the formula:

IIb

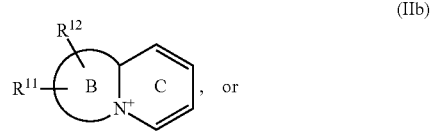

(IIb)

, or

IIc

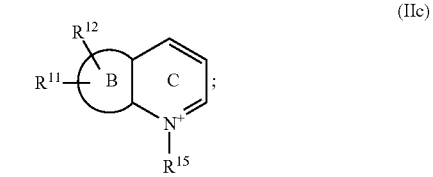

(IIc)

or a pharmaceutically acceptable salt thereof, wherein:

ring C is a ring formed by taking together $R^9$ and $R^{10}$, wherein ring C optionally comprises 1 to 2 ring nitrogen atoms in addition to the quaternary nitrogen;

$R^{11}$ is —(C$_0$-C$_4$ alkylene)-SO$_3^-$;

$R^{12}$ is selected from hydrogen, —(C$_0$-C$_4$ alkylene)-aryl, —(C$_0$-C$_4$ alkylene)-heteroaryl, —(C$_0$-C$_4$ alkylene)-carbocyclyl, and —(C$_0$-C$_4$ alkylene)-heterocyclyl; and $R^{15}$ is C$_1$-C$_4$ alkyl.

In an eighteenth embodiment, provided herein is a method of treating a disease characterized by amyloid aggregates comprising the step of administering to a subject in need thereof a compound of structural formula II or IIa, wherein $R^7$ is —SO$_2$—OH; and $R^8$ is —NH$_2$; and wherein the remaining variables are as described above for structural formula II or IIa. In some aspects of the eighteenth embodiment, $R^9$ and $R^{10}$ are both hydrogen, wherein the remaining variables are as described above for structural formula II or IIa.

In a nineteenth embodiment, provided herein is a method of treating a disease characterized by amyloid aggregates comprising the step of administering to a subject in need thereof a compound of structural formula II or IIa, wherein $R^7$ is —SO$_2$—OH; and ring B comprises a ring nitrogen bound to hydrogen; and wherein the remaining variables are as

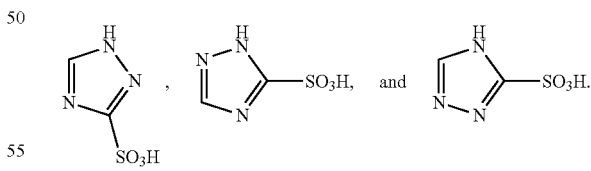

described above for structural formula II or IIa. Examples of such compounds are:

In a twentieth embodiment, provided herein is a method of treating a disease characterized by amyloid aggregates comprising the step of administering to a subject in need thereof a compound of structural formula II or IIa, wherein $R^7$ is —SO$_3^-$; and $R^9$ and $R^{10}$ are taken together with ring B to form a bicyclic, quaternary nitrogen-containing ring system; and wherein the remaining variables are as described above for structural formula II or IIa. In some aspect of the twentieth embodiment, the ring formed by $R^9$ and $R^{10}$ is substituted with up to two $C_1$-$C_4$ alkyl groups.

In a twenty-first embodiment, provided herein is a method of treating a disease characterized by amyloid aggregates comprising the step of administering to a subject in need thereof a compound of structural formula III:

(III)

or a pharmaceutically acceptable salt thereof, wherein:

ring D is phenyl, pyridyl, triazolyl, pyrazolyl, thiazolyl, triazinyl, pyrimidinyl, or thiophenyl;

q is 2, 3, or 4;

$R^{16}$ is selected from $(C_1$-$C_4)$alkyl, —$(C_1$-$C_4)$alkyl-COOR$^a$, $(C_1$-$C_4)$alkylSO$_3$H, —O$(C_1$-$C_4)$alkyl, —SO$_3$H, —NR$^a$R$^b$, —OR$^a$, —COOR$^a$, —COONR$^a$R$^b$, morpholinyl, pyrazolyl, isoxazolyl, phenyl, and dihydropyrazolyl, wherein each of said morpholinyl, pyrazolyl, isoxazolyl, and phenyl are optionally substituted with 1 to 3 groups selected from —NR$^c$R$^d$, SO$_3$H, $(C_1$-$C_4)$alkyl, and —COOR$^c$, and wherein said dihydropyrazolyl is optionally substituted with 1 to 3 groups selected from oxo, —NR$^c$R$^d$, SO$_3$H, $(C_1$-$C_4)$alkyl, and —COOR$^c$;

R$^a$ and R$^b$ are each independently hydrogen, $(C_1$-$C_4)$alkyl, or phenyl, wherein said phenyl is optionally substituted with 1 or 2 —NR$^c$R$^d$ groups; and R$^c$ and R$^d$ are each independently hydrogen or $(C_1$-$C_4)$alkyl.

In a twenty-second embodiment, $R^{16}$ in the compound of structural formula III of the present methods is selected from $(C_1$-$C_4)$alkyl; $(C_1$-$C_4)$alkylCOOH; $(C_1$-$C_4)$alkylSO$_3$H; —O$(C_1$-$C_4)$alkyl; —SO$_3$H; NH$_2$; —NH$(C_1$-$C_4)$alkyl, OH; COOH; —NHphenyl; —NHphenyl(NH$_2$); —COOCH$_3$; COON(CH$_3$)$_2$; morpholinyl; pyrazolyl substituted with 1 or 2 groups selected from $(C_1$-$C_4)$alkyl, NH$_2$, and COOEt; isoxazolyl substituted with 1 or 2 $(C_1$-$C_4)$alkyl) groups; phenyl substituted with 1 or 2 groups selected from $(C_1$-$C_4)$alkyl and SO$_3$H; and dihydropyrazolyl substituted with 1 or 2 groups selected from $(C_1$-$C_4)$alkyl, NH$_2$, oxo, and COOH, wherein the remaining variables are as described above for formula III.

In a twenty-third embodiment, provided herein is a method of treating a disease characterized by amyloid aggregates comprising the step of administering to a subject in need thereof a compound of structural formula IV:

(IV)

or a pharmaceutically acceptable salt thereof, wherein:

ring E is benzoimidazolyl, indolinyl, naphthalenyl, dihydrobenzooxazinyl-2-one, benzothiazolyl, thiazolopyrimidinyl-4-ium, or benzoxazolyl;

t is 2, 3, or 4;

$R^{17}$ is selected from $(C_1$-$C_4)$alkyl, —O$(C_1$-$C_4)$alkyl, —SO$_3$H, —$(C_1$-$C_4)$alkylSO$_3$H, —NR$^a$R$^b$, and phenyl, wherein said phenyl is optionally substituted with $(C_1$-$C_4)$alkyl or —NR$^a$R$^b$; and R$^a$ and R$^b$ are each independently hydrogen or $(C_1$-$C_4)$alkyl.

In a twenty-fourth embodiment, $R^{17}$ in the compound of structural formula IV of the present methods is selected from $(C_1$-$C_4)$alkyl, —SO$_3$H, —$(C_1$-$C_4)$alkylSO$_3$H, NH$_2$, and phenyl, wherein said phenyl is optionally substituted with NH$_2$, wherein the remaining variables are as described above for formula IV.

In a twenty-fifth embodiment, provided herein is a method of treating a disease characterized by amyloid aggregates comprising the step of administering to a subject in need thereof a compound as provided in Table 1, below. Neutral forms, salt forms, charged forms, hydrates, free base forms and tautomeric forms of those compounds, where applicable, are included.

TABLE 1

| Compound | Structure |
|---|---|
| 100 | ![structure](pyridine with 2-NH2 and 3-SO2OH) |
| 101 | ![structure](pyridine with 6-NH2 and 3-SO2OH) |
| 102 | ![structure](pyridine with 3-NH2 and 5-SO2OH) |
| 103 | ![structure](pyridine with 6-NH2 and 2-SO2OH) |
| 104 | ![structure](pyridine with 3-NH2 and 2-CH2CH2SO2OH) |
| 105 | ![structure](pyridine with 3-SO2H and 4-NHiPr) |
| 106 | ![structure](pyridine with 4-NH2 and 2-SO2OH) |

TABLE 1-continued
| Compound | Structure |
|---|---|
| 107 | 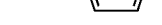 |
| 108 |  |
| 109 |  |
| 110 |  |
| 111 |  |
| 112 |  |
| 113 |  |
| 114 |  |
| 115 |  |
| 116 | 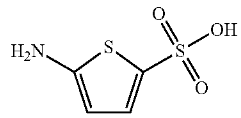 |
| 117 | 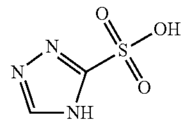 |
| 118 | 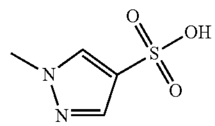 |
| 119 | 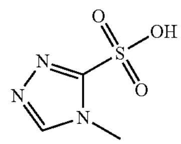 |
| 120 | 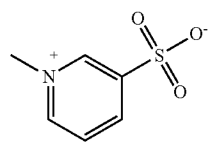 |
| 121 | 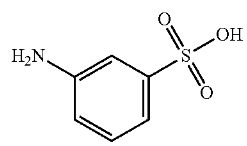 [SMILES: Nc1cccc(S(=O)(=O)O)c1] |
| 122 | 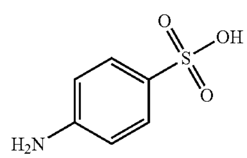 [SMILES: Nc1ccc(S(=O)(=O)O)cc1] |
| 123 | 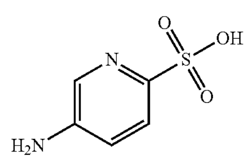 [SMILES: Nc1ccc(S(=O)(=O)O)nc1] |
| 124 | 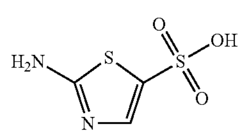 |
| 125 | 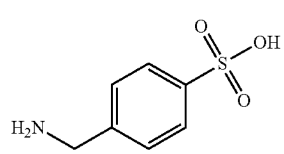 [SMILES: NCc1ccc(S(=O)(=O)O)cc1] |

TABLE 1-continued

| Compound | Structure |
|---|---|
| 126 | 2,5-diaminobenzenesulfonic acid |
| 127 | 2,4-diaminobenzenesulfonic acid |
| 128 | 3-amino-4-hydroxybenzenesulfonic acid |
| 129 | 3,5-dioxo-2,3,4,5-tetrahydro-1,2,4-triazine-6-sulfonic acid |
| 130 | 1H-benzimidazole-5-sulfonic acid |
| 131 | 2,3-dihydro-1H-indole-6-sulfonic acid |
| 132 | (4-amino-2-methylpyrimidin-5-yl)methanesulfonic acid |
| 133 | 1-methyl-1H-benzimidazole-2-sulfonic acid |
| 134 | 6-amino-9H-purine-8-sulfonic acid |
| 135 | 6-aminonaphthalene-2-sulfonic acid |

TABLE 1-continued

| Compound | Structure |
|---|---|
| 136 | 8-aminonaphthalene-2-sulfonic acid |
| 137 | 4-aminonaphthalene-1-sulfonic acid |
| 138 | 5-aminonaphthalene-1-sulfonic acid |
| 139 | 5-aminonaphthalene-2-sulfonic acid |
| 140 | 6-aminonaphthalene-1-sulfonic acid |
| 141 | 2-oxo-1,4-dihydro-2H-benzo[d][1,3]oxazine-6-sulfonic acid |
| 142 | 2-amino-1,3-benzothiazole-6-sulfonic acid |
| 143 | 3-amino-2-hydroxy-5-sulfobenzoic acid |

TABLE 1-continued

| Compound | Structure |
|---|---|
| 144 | 5,6-diamino-naphthalene-1-sulfonic acid |
| 145 | 1-propyl-1H-benzimidazole-2-sulfonic acid |
| 146 | 6-amino-naphthalene-2-sulfonic acid hydrate |
| 147 | 3-amino-7-methyl-benzo[d]isothiazole-5-sulfonic acid |
| 148 | 5,7-dimethyl-imidazo[1,2-a]pyrimidin-4-ium-2-sulfonate |
| 149 | sodium 7-amino-naphthalene-2-sulfonate |
| 150 | 4-(phenylamino)benzenesulfonic acid |
| 151 | methyl 4-methoxy-5-sulfo-thiophene-2-carboxylate |
| 152 | 4-(3,5-dimethyl-1H-pyrazol-1-yl)benzenesulfonic acid |
| 153 | 2-ethyl-5-(3-sulfonatophenyl)isoxazol-2-ium |
| 154 | 3-(3-methyl-5-oxo-4,5-dihydro-1H-pyrazol-1-yl)benzenesulfonic acid |
| 155 | 3-(3-amino-5-oxo-4,5-dihydro-1H-pyrazol-1-yl)benzenesulfonic acid |
| 156 | 2-(3-amino-5-oxo-4,5-dihydro-1H-pyrazol-1-yl)benzenesulfonic acid |
| 157 | 4-(3-amino-5-oxo-4,5-dihydro-1H-pyrazol-1-yl)benzenesulfonic acid |
| 158 | 1-(dimethylcarbamoyl)-4-(2-sulfonatoethyl)pyridin-1-ium |
| 159 | 4,6-diaminobenzene-1,3-disulfonic acid |

TABLE 1-continued

| Compound | Structure |
|---|---|
| 160 | (structure) |
| 161 | (structure) |
| 162 | (structure) |
| 163 | (structure) |
| 164 | (structure) |
| 165 | (structure) |
| 166 | (structure) |
| 167 | (structure) |
| 168 | (structure) |
| 169 | (structure) |
| 170 | (structure) |
| 171 | (structure) |
| 172 | (structure) |

3. Uses, Formulation, and Administration

In one aspect, the present disclosure provides the use of one or more compounds described herein, or a pharmaceutically acceptable salt thereof, for treating a disease characterized by amyloid aggregates. Also provided is the use of one or more compounds described herein, or a pharmaceutically acceptable salt thereof, for the manufacture of a medicament for treating a disease characterized by amyloid aggregates.

In one aspect, diseases characterized by amyloid aggregates include, but are not limited to, Alzheimer's disease including familial (hereditary) forms thereof, Down's syndrome dementia, Parkinson's Disease, Acute macular degeneration (AMD), glaucoma, Inclusion Body Myositis (IBM), traumatic brain injury, Lewy Bodies dementia, Huntington's disease, Nieman-Picks Type C, Cerebral Amyloid Angiopathy (CAA), Creutzfeldt-Jakob disease, AA Amyloidosis, AL Amyloidosis, ATTR amyloidosis, Familial amyloid polyneuropathy (FAP), Familial amyloid cardiomyopathy (FAC), Senile systemic amyloidosis, and prion disease. In one aspect, the disease characterized by amyloid aggregates is Alzheimer's disease.

Other diseases characterized by a pathophysiological link to amyloid deposition, formation and/or potential for prion-like self-propagation are also included in the methods described herein.

Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and croscarmellose sodium), polyethylene glycol, sodium carboxymethylcellulose, polyacrylates, waxes, polyethylene-polyoxypropylene-block polymers, polyethylene glycol and wool fat.

Method of administration can use an amount and a route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. For example, provided compounds may be formulated such that a dosage of between 0.01-100 mg/kg body weight/day of the compound can be administered to a patient receiving these compositions. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Method of administration to humans and other animals can be orally, rectally, parenterally, intracisternally, intravaginally, intraperitoneally, topically (as by powders, ointments, or drops), buccally, as an oral or nasal spray, or the like, depending on the severity of the infection being treated. In a more specific aspect, the method of administration is oral.

EXEMPLIFICATION

Synthetic Methods

Compounds described herein may be purchased commercially and/or prepared following the general methods described below.

Oxidation of Heteroaromatic Thiols

Heteroaromatic thiols e.g., 4-amino-5-aryl-3-thiol-4H-1,2,4-triazole can be oxidized from the appropriate thiol starting material using 30% $H_2O_2$ in aq. acetic acid at e.g., room temperature. See Scheme 1 below for a non-limiting representation that can be generally applied to related starting materials and products.

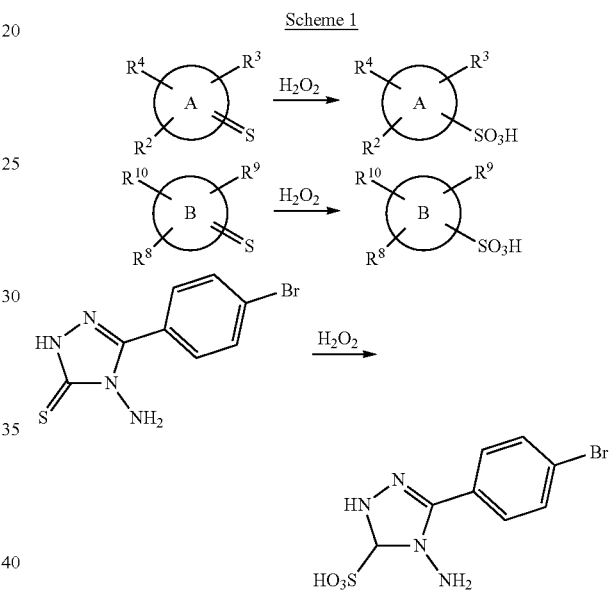

Sulfonation of Aminothiazoles

Aminoheterocycles e.g., aminothiazoles can be sulfonated by slowly adding to the aminoheterocycle small portions to chlorosulfonic acid cooled (e.g., at −5 deg Celsius (C)) while stirring e.g., within 30 minutes. After hydrogen chloride evolution is observed, the reaction mixture may then be stirred for 1 hour at room temperature. The reaction may be slowly poured on crushed ice and neutralized by cooled NaOH solution while temperature is maintained e.g., below 10 deg Celsius. The precipitate may be filtered and washed, e.g., with ethanol and water. See Scheme 2 below for a non-limiting representation that can be generally applied to related starting materials and products.

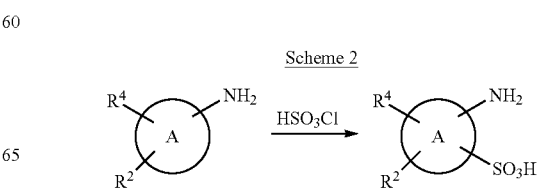

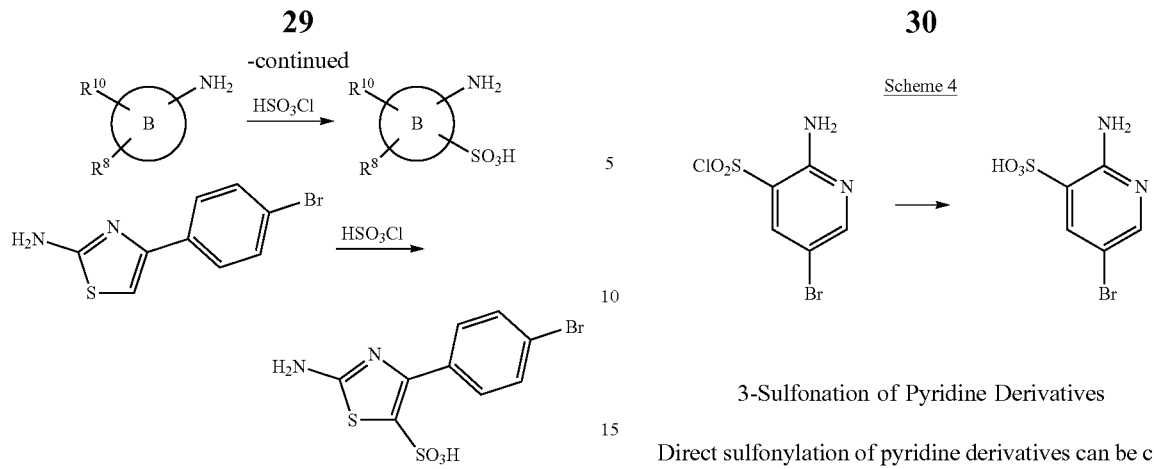

Deprotection of Benzylthio Groups Followed by Oxidation to Sulfonic Acids

Benzylthio groups may be converted to sulfonic acids using the following methods. A suspension of a benzylthio-compound in 50% aq. acetic acid may be oxidized by chlorine for 30 minutes at e.g., 5 deg Celsius. The product may be isolated via acidification with HCl. See Scheme 3 below for a non-limiting representation that can be generally applied to related starting materials and products.

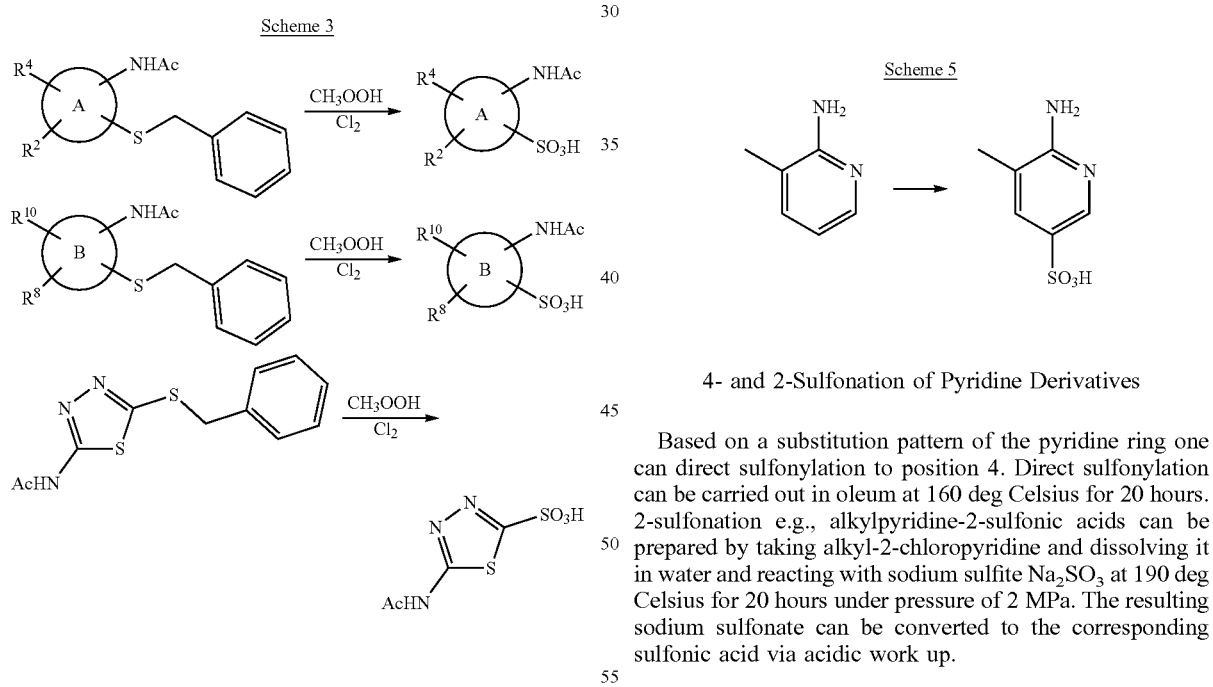

Synthesis of 2-(alkyl)amino-5-halo-3-pyridinesulfonic Acid

The corresponding 2-(alkyl)amino-5-halo-3-pyridine-sulfonylchloride or sulfonamide can be subjected to acidic hydrolysis with HCl in aqueous solution with added acetonitrile if needed to solubilize the compound completely. The reaction can be carried out in room temperature overnight to the completion. See Scheme 4 below for a non-limiting representation that can be generally applied to related starting materials and products.

3-Sulfonation of Pyridine Derivatives

Direct sulfonylation of pyridine derivatives can be carried out in ethanol solution with conc. Sulfuric acid and metal Aluminum for 5 hrs at a temperature of 210 deg C.

An alternative method to sulfonate a pyridine derivative is to add the pyridine derivative portionwise to oleum (sulfuric acid mixture with sulfur trioxide) over 30 min. The resulting solution can then be heated to 140 deg C for 4 hours. The reaction mixture can then be poured onto ice and the mixture can then be stirred in an ice bath (ice with salt) for another 2 hours. The resulted suspension can then be filtered, and the solid washed with water and dried under suction. See Scheme 5 below for a non-limiting representation that can be generally applied to related starting materials and products.

4- and 2-Sulfonation of Pyridine Derivatives

Based on a substitution pattern of the pyridine ring one can direct sulfonylation to position 4. Direct sulfonylation can be carried out in oleum at 160 deg Celsius for 20 hours. 2-sulfonation e.g., alkylpyridine-2-sulfonic acids can be prepared by taking alkyl-2-chloropyridine and dissolving it in water and reacting with sodium sulfite $Na_2SO_3$ at 190 deg Celsius for 20 hours under pressure of 2 MPa. The resulting sodium sulfonate can be converted to the corresponding sulfonic acid via acidic work up.

Sulfonation of Pyrimidine Derivatives

A pyrimidine derivative can be slowly dissolved in monochlorosulfuric acid at room temperature and then stirred at 150 deg Celsius for 8 hours. The reaction mixture is cooled and worked up in a similar way as described for pyridine-derived compounds above. The corresponding sulfonylchloride can then be hydrolyzed in water into the corresponding sulfonic acid. See Scheme 6 below for a non-limiting representation that can be generally applied to related starting materials and products.

Scheme 6.

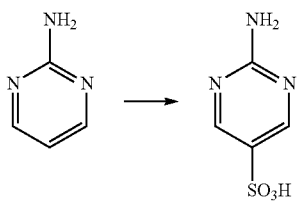

Substitution of Heteroaromatic Halides with Substituted Amines

Corresponding halo-compounds can be reacted with an alcoholic solution of the corresponding amine. See Scheme 7 below for a non-limiting representation that can be generally applied to related starting materials and products.

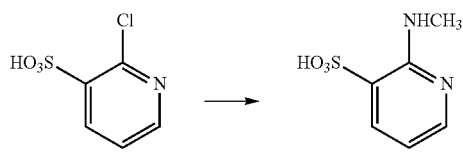 [SMILES: O=S(=O)(O)c1cccnc1Cl ; CNc1ncccc1S(=O)(=O)O]

Pd-Catalyzed Amination

Palladium catalyzed amination may be carried out on five-membered, six-membered, and aryl-fused heteroaromatic compounds described herein. Such methods are well-known to those skill in the art and include, but are not limited to, reacting an amine with an aromatic halide, triflate, or the like (designated by X) with a Pd(0) species, or Pd(0) formed in situ from Pd(II), and ligand optionally in the presence of base (e.g., LHMDS) to form the corresponding amine. A precatalyst may also be added. A representative scheme is shown below as Scheme 8.

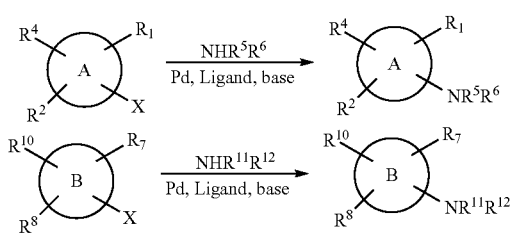

Palladium species are known in the art and include e.g., palladium(II) catalysts (e.g., bis(acetonitrile)palladium(II) chloride, palladium(II) acetate, palladium(II) bromide, palladium(II) chloride, palladium(II) trifluoroacetate, tetrakis (acetonitrile)palladium (II) tetrafluoroborate, [1,2-bis(diphenylphosphino)ethane] dichloropalladium(II), bis (triethylphosphine)palladium(II) chloride, bis (triphenylphosphine) palladium(II) acetate, bis (triphenylphosphine)palladium(II) chloride, bis[tri(o-tolyl) phosphine]palladium(II) chloride, dichlorobis (tricyclohexylphosphine)palladium(II), trans-benzyl (chloro) bis(triphenylphosphine)palladium(II), and the like or commercially available palladium(0) catalysts (e.g., tris (dibenzylideneacetone)dipalladium(0), bis(tricyclohexylphosphine) palladium(0), bis(tri-t-butylphosphine)palladium(0), bis[1,2-bis(diphenylphosphino)ethane] palladium (0), tetrakis(triphenylphosphine)palladium(0), and the like.

Ligands and/or precatalysts for use in facilitating palladium-mediated aminations may be monodentate or bidentate ligands. Examples include, but are not limited to, RuPhos, t-BuXPhos, BrettPhos, AdBrettPhos, tBuBrett-Phose, Me$_4$tBuXPhos, JohnPhos, and the like. Buchwald-Hartwig-type palladacycles may also be used.

Molecular Modeling

Molecular modeling to determine the degree to which the compounds used in the methods described herein can bind to ß-amyloid can be performed using the Schrödinger suite (Schrödinger Suite, 2015-3; Schrödinger, LLC: New York, N.Y., 2015). Molecular dynamics simulations can be run using the algorithms described in Desmond Bowers, K. J. et al. Scalable Algorithms for Molecular Dynamics Simulations on Commodity Clusters. SC Conference, Proceedings of the ACMIEEE, IEEE 43-56 (2006). The simulations can be run on GeForce GTX Titan Black GPU cards. The OPLS 3.0 force field (Shivakumar, D., Harder, E., Damm, W., Friesner, R. A. & Sherman, W. Improving the Prediction of Absolute Solvation Free Energies Using the Next Generation OPLS Force Field. J. Chem. Theory Comput. 8, 2553-2558 (2012)) can be used to model all interactions between the compounds used herein and ß-amyloid, and the SPC model can be used for waters. The 1IYT Aß42 NMR structure from the PDB can be used as a starting point for MD simulations. This structure is primarily alpha helical and is representative of the peptide in an apolar environment. A 20 Angstrom box of water or a mixed solvent box of 1% compound in water can be added around the peptide using Schrödinger system setup tools. Ions can then be added to neutralize the charge of the entire system. Simulations were equilibrated and run under NPT conditions (constant pressure and temperature) with periodic boundary conditions. The Nose-Hoover Thermostat and Martina-Tobias-Klein barostat can be used to control temperature and pressure, respectively. Simulations can be run in replicates of 3 for 100 nanoseconds each, and results compiled for analysis. Principal component analysis can be performed using ProDy (Bakan, A., Meireles, L. M. & Bahar, I. ProDy: protein dynamics inferred from theory and experiments. Bioinformatics (Oxford, England) 27, 1575-1577 (2011)) and plotted using custom python scripts.

Ion Mobility Mass Spectrometry (IMS MS)

Ion Mobility Mass Spectrometry can be used to assay the interaction between the compounds used in the present invention and beta-amyloid, namely amyloid beta (1-42), (or Aß42), amyloid beta (1-40) and pGlu-amyloid.

The conditions used for mass spectrometry can be as follows: Waters Synapt G2-S, positive polarity in sensitivity mode, capillary=2.5 kV, nebulizer=2 mbar, source temperature=80° C., desolvation temperature=60° C., sample cone setting=35 V, source offset setting=60 V, mass range=500 to 4000 m/z. These conditions can be maintained throughout the study to ensure consistency of the data and to avoid influencing the detection of oligomers due to preferential ionization conditions.

Samples can be directly infused into the mass spectrometer at a flow rate of 10 µL/min using a PM-1000 Syringe Pump and Hamilton 1 mL Syringe. The data acquisition of the amyloid peptide can be performed using a Waters Synapt G2-S quadrupole time of flight mass spectrometer (Q-TOF MS) with traveling wave ion mobility (Waters Corp. 34 Maple Street Milford, Mass. 01757). The data can be acquired using the systems sensitivity mode to allow for the detection of the less abundant oligomers. Samples can be infused at room temperature.

Sample Preparation

One mg of recombinant human β-amyloid peptide (1-42) from BioLegend (99% purity, cat: 843801) can be reconstituted in 200 µL of Fisher Optima LC/MS grade water (cat: W6-1) and vortexed vigorously for 2 minutes to solubilize the peptide creating a 5 mg/mL solution. Samples can then be diluted to a final concentration of 22 pmol/µL prior to incubation. The sample mixtures can then be incubated at room temperature for 0, 4 and 24 hours, respectively. When the acquisition of the incubated samples is completed the raw data can be analyzed using the Waters MassLynx v2.4 suite with DriftScover v2.7 to visualize drift times for the peptide.

4β42 Species Characterization

Aß42 species characterization using IMS MS can be performed by direct infusion of the peptide at 22 pmol/µL in $H_2O$. The peptide can be prepared in $H_2O$ to maintain the native state conformation of the peptide for the ion mobility data acquisition. Ion mobility data acquisition can be performed to detect and characterize the conformational changes of the native state monomer and any oligomers that may have formed during the incubation.

Binding Assay

The activity of the compounds utilized in the methods described herein can be assayed by measuring the binding of those compounds to ß-amyloid. Data acquisition can be performed using a Waters Synapt G2-S quadrupole time of flight mass spectrometer (Q-TOF MS) with traveling wave ion mobility (Waters Corp. 34 Maple Street Milford, Mass. 01757). The data can be acquired using the systems sensitivity mode to allow for the detection of the less abundant oligomers. Samples can be infused at room temperature due to lower solubility of the peptide at body temperature (37° C.).

One mg of compound can be reconstituted in 1 mL of Fisher Optima LC/MS grade water (cat: W6-1) and vortexed vigorously for 2 minutes until completely dissolved. The sample can be then diluted to create a 220 pmol/µL, 2200 pmol/µL, and 22,000 pmol/µL solutions to perform binding experiments to Aß42 with 10-, 100-, and 1000-fold molar excess of tested compound.

One mg of recombinant human β-Amyloid Peptide (1-42) from BioLegend can be reconstituted in 200 µL of Fisher Optima LC/MS grade water and vortexed vigorously to solubilize the peptide creating a 5 mg/mL solution. Samples can be then diluted to a final concentration of 44 pmol/µL prior to mixing (1:1) with test compound solution. Final concentrations were 22 pmol/µL for human β-Amyloid Peptide (1-42) and 1100 pmol/µL for test compounds.

The data acquisition was performed using a Waters time of flight mass spectrometer (Q-TOF Micro). The data was acquired using the scanning mode to allow for the detection of the peptide. Samples were infused at room temperature.

The mass spectrometer conditions were maintained throughout the study to ensure consistency of the data. The Waters Q-TOF conditions were as follows:

| Positive Polarity in sensitivity mode | |
| --- | --- |
| Capillary | 3.5 kV |
| Desolvation gas flow | 500 L/Hr |
| Cone gas flow | 50 L/Hr |
| Source Temperature | 150° C. |
| Desolvation Temperature | 60° C. |
| Sample cone setting | 35 V |
| Extraction cone setting | 3 V |
| Mass Range | 1475 to 2000 m/z |

Samples were directly infused into the mass spectrometer at a flow rate of 20 µL/min using in-build Syringe Pump and Hamilton 1 mL Syringe and the acquisition time was kept 2 minutes. The results for Compounds 117-172 are shown in Table 2, below:

TABLE 2

Number of Molecules Bound to Aβ1-42

| Compound | # of Molecules Bound to Aβ |
| --- | --- |
| 117 | 3 |
| 118 | 1 |
| 119 | 0 |
| 120 | 8 |
| 121 | 0 |
| 122 | 0 |
| 123 | ND |
| 124 | 3 |
| 125 | 0 |
| 126 | 1 |
| 127 | 0 |
| 128 | 0 |
| 129 | ND |
| 130 | 0 |
| 131 | 0 |
| 132 | ND |
| 133 | 0 |
| 134 | 2 |
| 135 | 0 |
| 136 | 0 |
| 137 | 0 |
| 138 | 0 |
| 139 | 0 |
| 140 | 0 |
| 141 | 0 |
| 142 | 2 |
| 143 | 0 |
| 144 | 0 |
| 145 | 0 |
| 146 | 0 |
| 147 | ND |
| 148 | 5 |
| 149 | 0 |
| 150 | 0 |
| 151 | 0 |
| 152 | 1 |
| 153 | 5 |
| 154 | 1 |
| 155 | ND |
| 156 | ND |
| 157 | ND |
| 158 | 0 |
| 159 | ND |
| 160 | 1 |
| 161 | 0 |
| 162 | ND |
| 163 | 0 |
| 164 | 0 |
| 165 | 1 |
| 166 | 2 |

TABLE 2-continued

Number of Molecules Bound to Aβ1-42

| Compound | # of Molecules Bound to Aβ |
|---|---|
| 167 | 0 |
| 168 | 0 |
| 169 | ND |
| 170 | 6 |
| 171 | 7 |
| 172 | 0 |

Short Term Treatment in Adult Transgenic CRND8 Mice Overexpressing βAPP

Transgenic mice, TgCRND8, expressing the human amyloid precursor protein (hAPP) develop a pathology resembling Alzheimer's disease. In particular, high levels of Aβ40 and Aβ42 have been documented in the plasma and the brain of these animals at 8-9 weeks of age, followed by early accumulation of amyloid plaques similar to the senile plaques observed in AD patients. These animals also display progressive cognitive deficits that parallel the appearance of degenerative changes. See, e.g., (Chishti, et al., J. Biol. Chem. 276, 21562-70 (2001).

The short term therapeutic effect of the compounds described herein can be studied by administration over a 14 or 28 day period at the end of which the levels of Aβ peptides in the plasma and brain of TgCRND8 animals are then determined.

Male and female transgenic mice from the $3^{rd}$ and $4^{th}$ B6C3F1 generations can be used and given daily subcutaneous or oral administrations of one of a series of compounds for 14 or 28 days. The following abbreviations can be used to designate these animals from the $3^{rd}$ and 4th generation backcross in the present protocol: TgCRND8-2.B6C3F1($N_3$); TgCRND8-2.B6C3F1($N_4$).

Baseline animals (control group) may consist of naive TgCRND8-2. B6C3F1($N_3$) at 11±1 weeks of age. These mice can be used to determine the Aβ levels in the plasma and brain of naive transgenic animals at the initiation of treatment.

Starting at 11 weeks of age (±1 week) animals receive daily administration of their respective treatment for a period of 14 or 28 days, at a dose of 250 mg/kg at 10 ml/kg of compounds, or of vehicle only (control group 2) or 1% methyl cellulose only (control group 3). The route of administration can be subcutaneous for water-soluble compounds and oral for compounds solubilized in methylcellulose 1% (MC 1%). At the end of the treatment periods, plasma and perfused brains are collected for quantification of Aβ levels.

All animals will be examined daily for signs of ill health when handled in the morning for their daily treatment and twice a day for mortality checks (once daily during weekends and holidays). Detailed examinations are then performed on the treatment initiation, weekly during the study, and once before terminal procedures. More frequent observations can be undertaken when considered appropriate. Death and all individual clinical signs will be individually recorded. Individual body weights are recorded at randomization, once weekly during the study, and once before terminal procedures.

At 11±1 weeks of age for the Baseline group, and 24 hours after the end of the treatment period (14 or 28 days) for the other animals including control Groups 2 and 3, animals are sacrificed and samples collected. An approximate blood volume of 500 μl will be collected from the orbital sinus and kept on ice until centrifugation at 4° C. at a minimum speed of 3,000 rpm for 10 minutes. Plasma samples are immediately frozen and stored at −80° C. pending analysis. The brains are then removed, frozen, and stored at −80° C. prior to analysis.

Brains are weighed, frozen and homogenized with 4 volumes of ice cold 50 mM Tris-Cl pH 8.0 buffer with protease inhibitor cocktail (4 mL of buffer for 1 g of wet brain). Samples are spun at 15000 g for 20 minutes and the supernatants are transferred to fresh tubes. One hundred fifty (150) μl from each supernatant are then mixed with 250 μl of 8M guanidine-HCL/50 mM Tris-HCL pH 8.0 (ratio of 0.6 vol supernatant: 1 vol 8M guanidium/Tris-HCL 50 mM pH8.0) and 400 μL 5 M guanidium/Tris-HCl 50 mM pH8.0 are added. The tubes are vortexed for 30 seconds and frozen at −80° C. In parallel, pellets are treated with 7 volumes of 5 M guanidine-HCL/50 mM Tris-HCL pH 8.0 (7 mL of guanidine for 1 g of wet brain), vortexed for 30 seconds and frozen at −80° C. Samples are thawed at room temperature, sonicated at 80° C. for 15 minutes and frozen again. This cycle can then be repeated 3 times to ensure homogeneity and samples were returned to −80° C. prior to analysis.

Aβ levels are evaluated in plasma and brain samples by ELISA using Human Aβ40 and Aβ42 Fluorometric ELISA kits from Biosource (Cat. No. 89-344 and 89-348) according to manufacturer's recommended procedures. Samples are thawed at room temperature, sonicated for 5 minutes at 80° C. (sonication for brain homogenates; no sonication for plasma samples) and kept on ice. Aβ peptides are captured using 100 μl of the diluted samples to the plate and incubated without shaking at 4° C. overnight. The samples are aspirated and the wells are rinsed 4 times with wash buffer obtained from the Biosource ELISA kit. The anti-Aβ40 or anti-Aβ42 rabbit polyclonal antiserum (specific for the Aβ40 or Aβ42 peptide) is added (100 μl) and the plate is incubated at room temperature for 2 hours with shaking. The wells are aspirated and washed 4 times before adding 100 μL of the alkaline phosphatase labeled anti-rabbit antibody and incubating at room temperature for 2 hours with shaking. The plates are then rinsed 5 times and the fluorescent substrate (100 μL) is added to the plate. The plate is incubated for 35 minutes at room temperature and the plate can then be read using a titer plate reader at an excitation wavelength of 460 nm and emission at 560 nm.

Compounds can be scored based on their ability to modulate levels of Aβ peptides in the plasma and the cerebral soluble/insoluble levels in the brain. Levels of Aβ observed in the plasma and brain of treated animals can be normalized using values from vehicle-treated (water) or methylcellulose-treated control groups and can be ranked according to the strength of the pharmacological effect.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) that may be cited throughout this application are hereby expressly incorporated herein in their entireties by reference. Unless otherwise defined, all technical and scientific terms used herein are accorded the meaning commonly known to one with ordinary skill in the art.

The invention claimed is:
1. A method of treating Alzheimer's disease comprising the step of administering to a subject in need thereof a compound selected from:
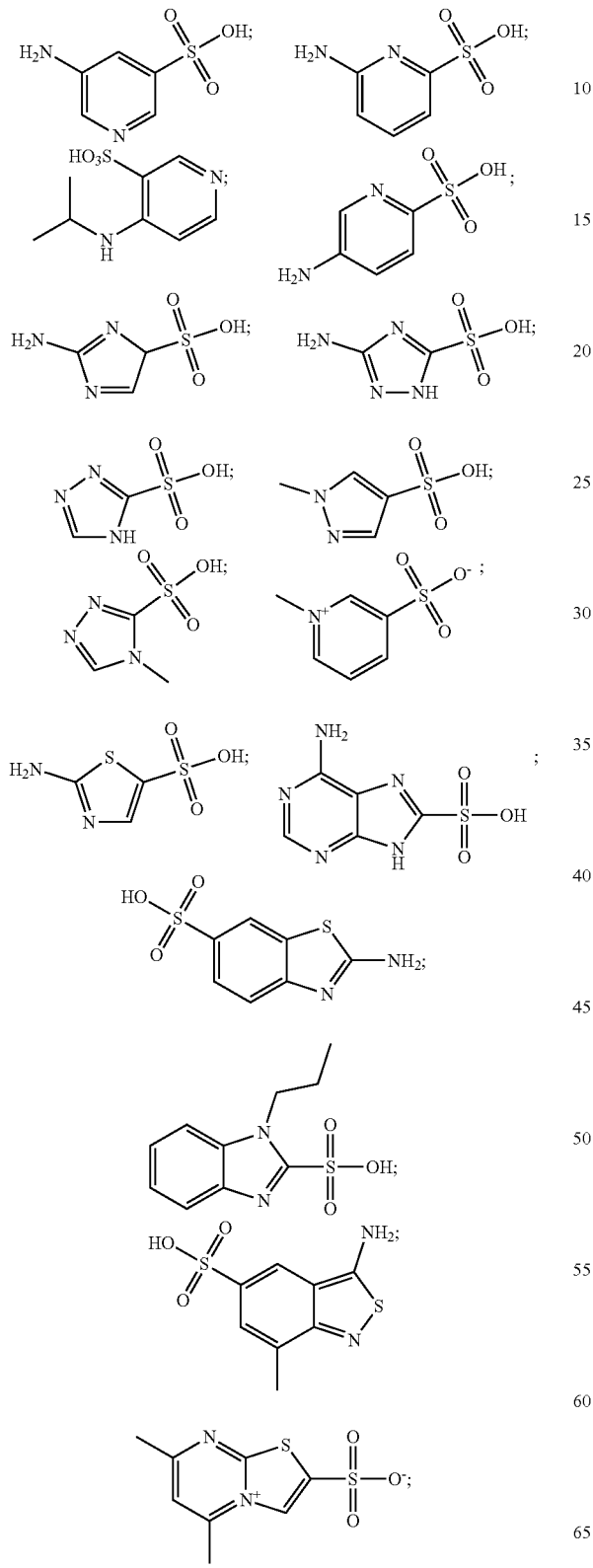
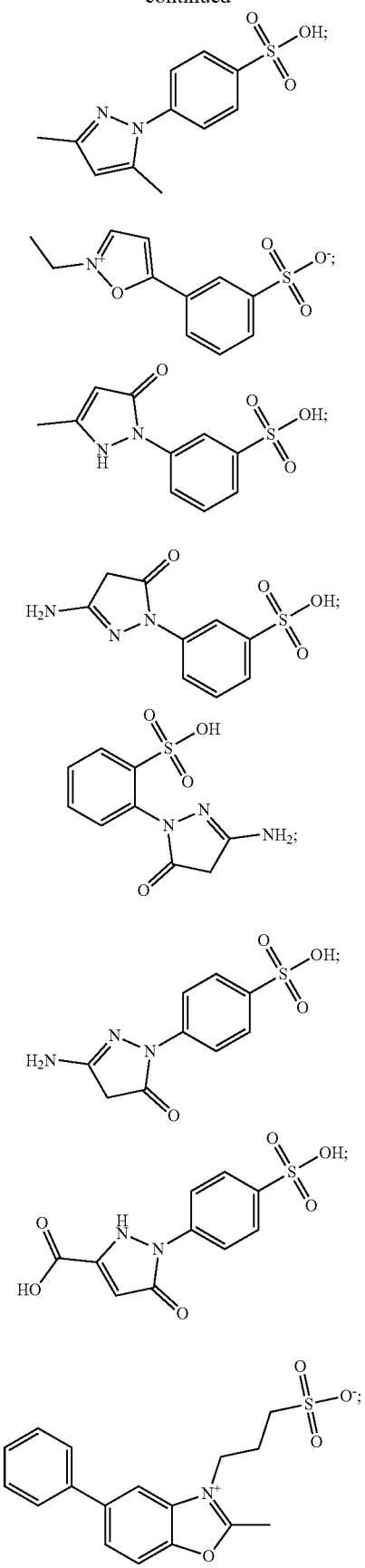

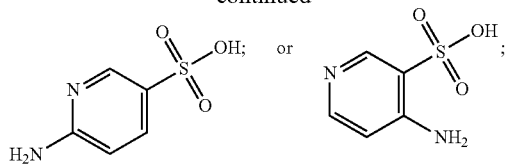

or a pharmaceutically acceptable salt of any of the foregoing.

2. The method of claim 1, wherein the compound is selected from:

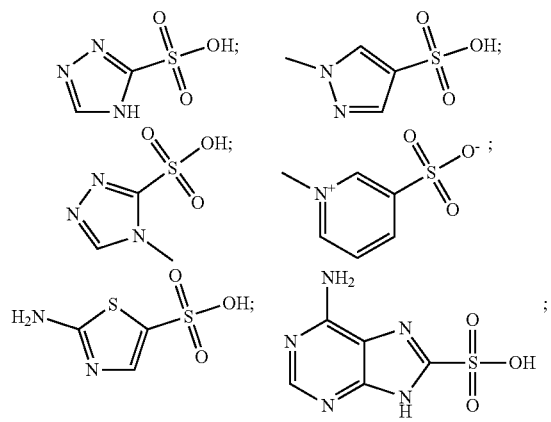

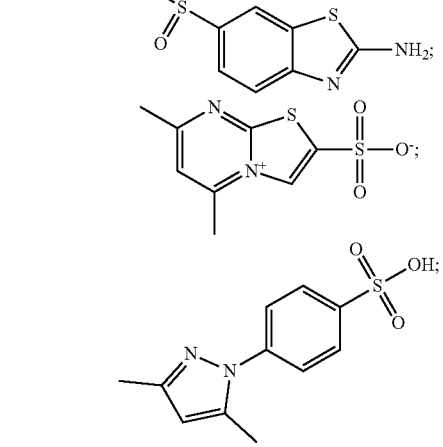

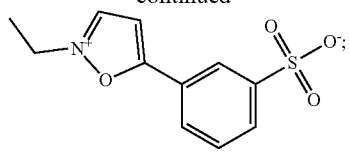

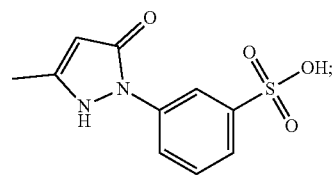

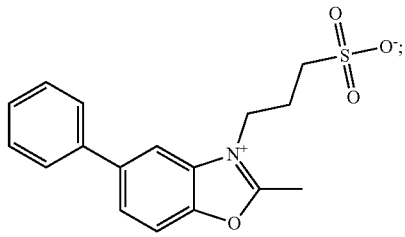

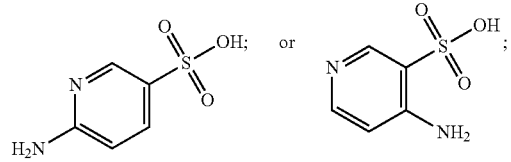 [SMILES: Nc1ccc(S(=O)(=O)O)cn1 ; Nc1ccncc1S(=O)(=O)O]

or a pharmaceutically acceptable salt of any of the foregoing.

3. The method of claim 1, wherein the compound is formulated into a pharmaceutically acceptable composition additionally comprising a pharmaceutically acceptable carrier.

4. The method of claim 2, wherein the compound is formulated into a pharmaceutically acceptable composition additionally comprising a pharmaceutically acceptable carrier.

* * * * *